US 10,646,260 B2

United States Patent
Abbasi

(10) Patent No.: US 10,646,260 B2
(45) Date of Patent: May 12, 2020

(54) EXTENSION READY SPINAL SUPPORT SYSTEMS

(71) Applicant: Advance Research System, LLC, Edina, MN (US)

(72) Inventor: Hamid R. Abbasi, Edina, MN (US)

(73) Assignee: Advance Research System, LLC, Edina, MN (US)

( * ) Notice: Subject to any disclaimer, the term of this patent is extended or adjusted under 35 U.S.C. 154(b) by 30 days.

(21) Appl. No.: 15/970,368

(22) Filed: May 3, 2018

(65) Prior Publication Data

US 2018/0317972 A1 Nov. 8, 2018

Related U.S. Application Data

(60) Provisional application No. 62/500,820, filed on May 3, 2017, provisional application No. 62/500,719, filed on May 3, 2017.

(51) Int. Cl.
*A61B 17/70* (2006.01)
*A61B 17/86* (2006.01)
*A61B 17/56* (2006.01)

(52) U.S. Cl.
CPC ...... *A61B 17/7032* (2013.01); *A61B 17/7034* (2013.01); *A61B 17/7037* (2013.01);
(Continued)

(58) Field of Classification Search
CPC ............ A61B 17/7032; A61B 17/7034; A61B 17/7037; A61B 17/7049; A61B 17/8605;
(Continued)

(56) References Cited

U.S. PATENT DOCUMENTS 5,261,912 A   11/1993   Frigg
5,520,690 A   5/1996    Errico et al.
(Continued)

FOREIGN PATENT DOCUMENTS

KR   10-2010-0119303   11/2010
WO   WO2010/028287    3/2010
(Continued)

*Primary Examiner* — Jacqueline T Johanas
*Assistant Examiner* — David C Comstock
(74) *Attorney, Agent, or Firm* — Christensen, Fonder, Dardi & Herbert PLLC

(57) ABSTRACT

An "extension ready" spinal support system that enables the extension to be accomplished with minimal disturbance to an existing spinal support structure to which the extension system is coupled. In some embodiments, the existing spinal support rod and pedicle screws can remain intact while extension subassemblies are mounted directly to the existing base rod receptacles. The extension subassemblies include a skirt portion that surrounds and engages the existing base receptacle to prevent splaying of the base receptacle. Additional resistance to splaying may be provided by a canted thread arrangement between the skirt and the base receptacle. In some embodiments, the extension receptacle is provided with a low profile (i.e., shortened axial length from the base rod receptacle) by providing a monoaxial rotation structure that rotates about but does not pitch relative to the extension axis and is shorter relative to polyaxial rotation structures.

20 Claims, 12 Drawing Sheets

(52) U.S. Cl.
CPC ...... *A61B 17/7049* (2013.01); *A61B 17/8605* (2013.01); *A61B 17/7002* (2013.01); *A61B 17/7074* (2013.01); *A61B 2017/564* (2013.01)

(58) Field of Classification Search
CPC ............ A61B 17/7002; A61B 17/7074; A61B 2017/564
USPC ....... 606/264, 265, 266, 267, 270, 271, 273, 606/278
See application file for complete search history.

(56) References Cited

U.S. PATENT DOCUMENTS

| | | | |
|---|---|---|---|
| 5,669,911 | A | 9/1997 | Errico et al. |
| 5,672,176 | A | 9/1997 | Biedermann et al. |
| 5,782,833 | A | 7/1998 | Haider |
| 5,882,350 | A | 3/1999 | Ralph et al. |
| 5,964,760 | A | 10/1999 | Richelsoph |
| 6,074,391 | A | 6/2000 | Metz-Stavenhagen et al. |
| 6,248,105 | B1 | 6/2001 | Schläpfer et al. |
| 6,296,642 | B1 * | 10/2001 | Morrison ............ A61B 17/7032 606/300 |
| 6,440,137 | B1 | 8/2002 | Horvath et al. |
| 6,520,963 | B1 | 2/2003 | McKinley |
| 6,585,737 | B1 | 7/2003 | Baccelli et al. |
| 6,835,196 | B2 | 12/2004 | Biedermann et al. |
| 6,843,791 | B2 | 1/2005 | Serhan |
| 7,156,850 | B2 | 1/2007 | Kim |
| 7,291,151 | B2 | 11/2007 | Alvarez |
| 7,445,627 | B2 | 11/2008 | Hawkes et al. |
| 7,896,902 | B2 | 3/2011 | Jeon et al. |
| RE42,545 | E | 7/2011 | Ralph et al. |
| 8,083,776 | B2 | 12/2011 | Alvarez |
| 8,257,402 | B2 | 9/2012 | Jackson |
| 8,273,109 | B2 | 9/2012 | Jackson |
| 8,337,532 | B1 * | 12/2012 | McLean ............ A61B 17/7011 606/279 |
| 8,702,758 | B2 * | 4/2014 | Wang ................ A61B 17/8085 606/257 |
| 8,747,405 | B2 | 6/2014 | Belliard |
| 8,852,241 | B2 | 10/2014 | Datta |
| 8,870,928 | B2 | 10/2014 | Jackson |
| 9,023,087 | B2 | 5/2015 | Frankel et al. |
| 9,277,950 | B2 | 3/2016 | Buttermann |
| 9,427,260 | B2 | 8/2016 | Juchno et al. |
| 9,451,994 | B1 | 9/2016 | Whipple et al. |
| 9,510,867 | B2 | 12/2016 | Garamszegi |
| 10,149,702 | B2 | 12/2018 | Ewer et al. |
| 2002/0082602 | A1 * | 6/2002 | Biedermann ...... A61B 17/7032 606/271 |
| 2003/0125741 | A1 * | 7/2003 | Biedermann ...... A61B 17/7032 606/278 |
| 2004/0249380 | A1 * | 12/2004 | Glascott ............ A61B 17/7032 606/278 |
| 2006/0079895 | A1 | 4/2006 | McLeer |
| 2007/0055238 | A1 | 3/2007 | Biedermann et al. |
| 2008/0287998 | A1 | 11/2008 | Doubler et al. |
| 2010/0094353 | A1 | 4/2010 | Shim et al. |
| 2010/0160981 | A1 * | 6/2010 | Butler ................ A61B 17/7037 606/308 |
| 2011/0190821 | A1 | 8/2011 | Chin et al. |
| 2012/0130436 | A1 * | 5/2012 | Haskins ............ A61B 17/7032 606/305 |
| 2012/0215263 | A1 | 8/2012 | Lee |
| 2012/0271365 | A1 | 10/2012 | Daubs et al. |
| 2013/0345755 | A1 * | 12/2013 | Prajapati ............ A61B 17/7007 606/273 |
| 2014/0094849 | A1 | 4/2014 | Spratt et al. |
| 2014/0121703 | A1 | 5/2014 | Jackson et al. |
| 2014/0135839 | A1 | 5/2014 | Frankel et al. |
| 2014/0135854 | A1 | 5/2014 | Dec et al. |
| 2014/0148858 | A1 * | 5/2014 | Dant .................. A61B 17/7007 606/278 |
| 2014/0316475 | A1 | 10/2014 | Parikh et al. |
| 2016/0242817 | A1 | 8/2016 | Abbasi |
| 2018/0228518 | A1 * | 8/2018 | Carruth ............. A61B 17/7049 |

FOREIGN PATENT DOCUMENTS

| | | |
|---|---|---|
| WO | WO2010/037098 | 4/2010 |
| WO | WO2014/052117 | 4/2014 |
| WO | WO2014/138736 | 9/2014 |

* cited by examiner

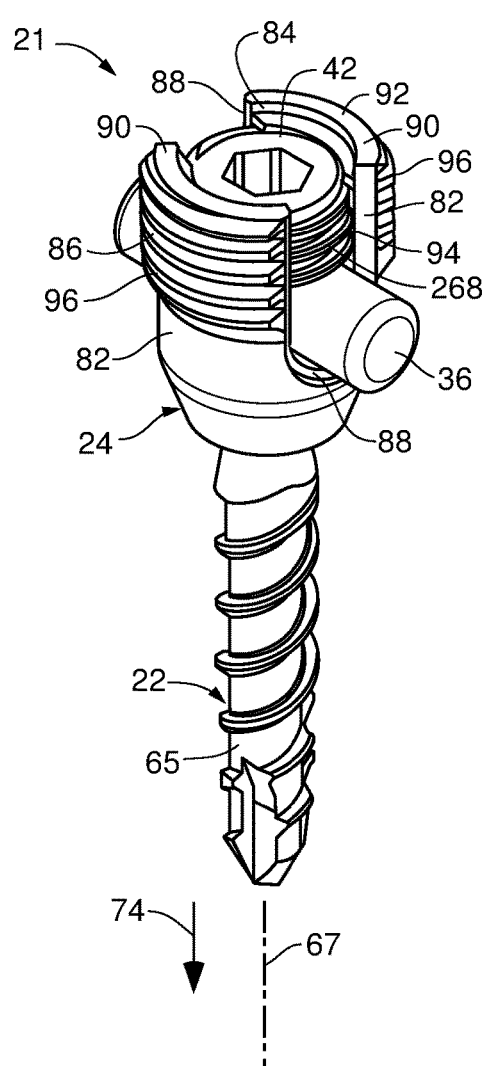
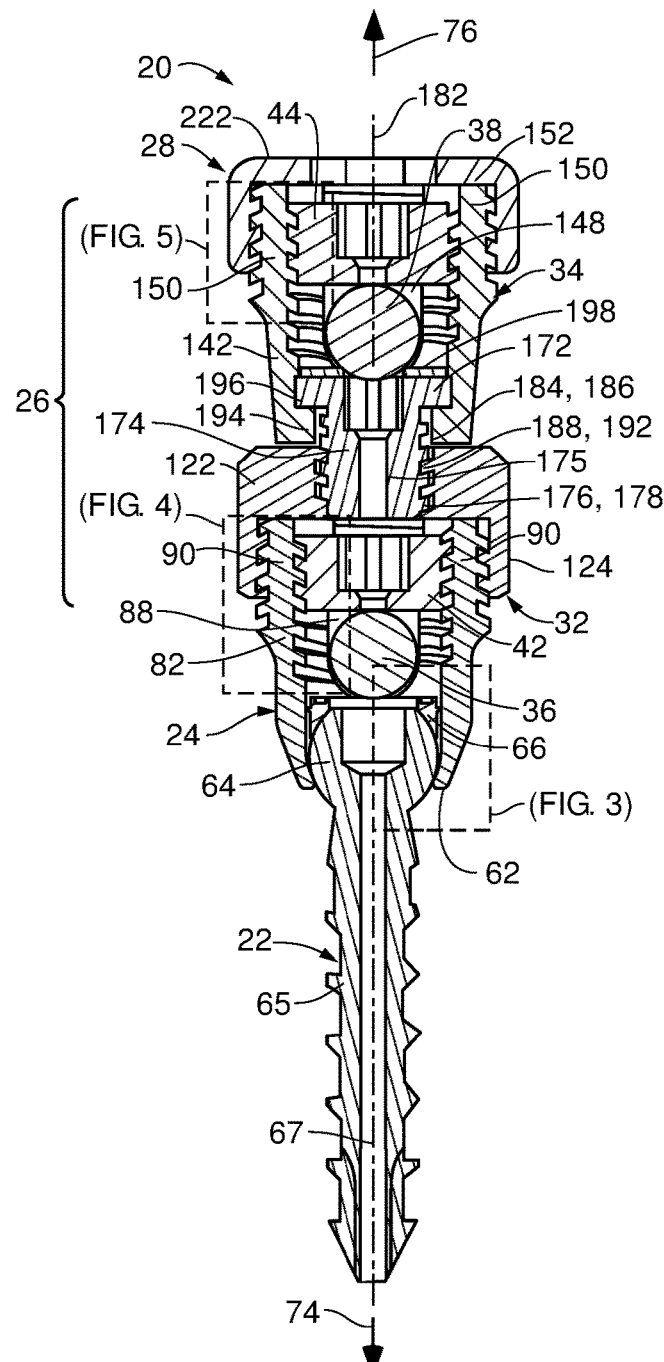
FIG. 1
FIG. 2

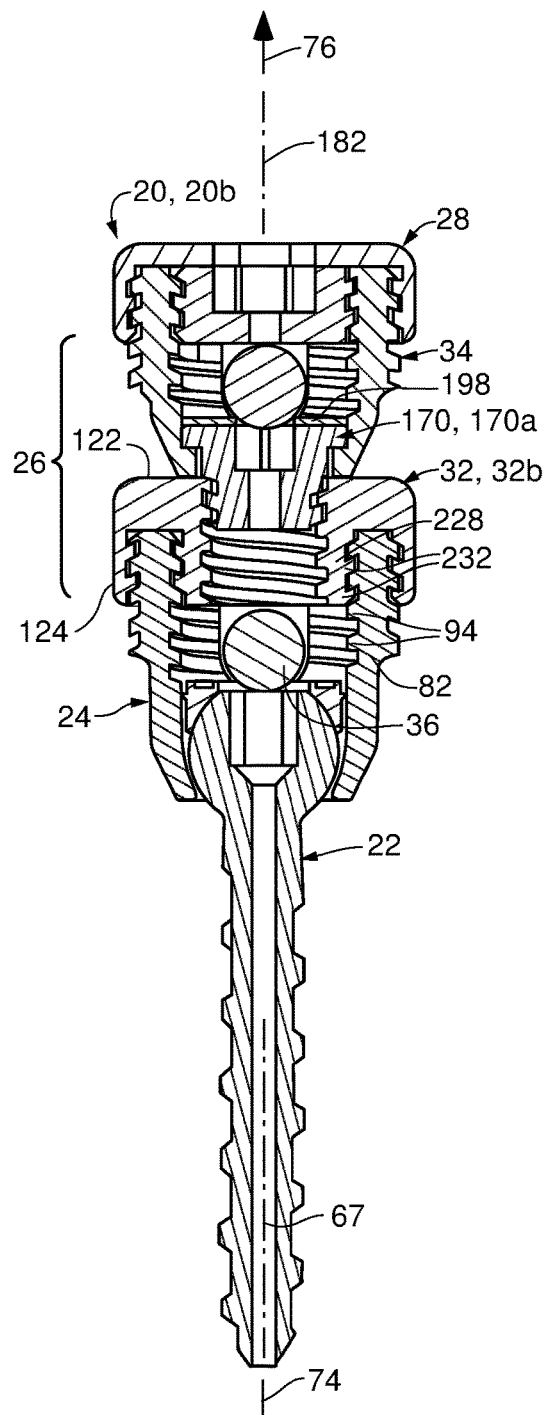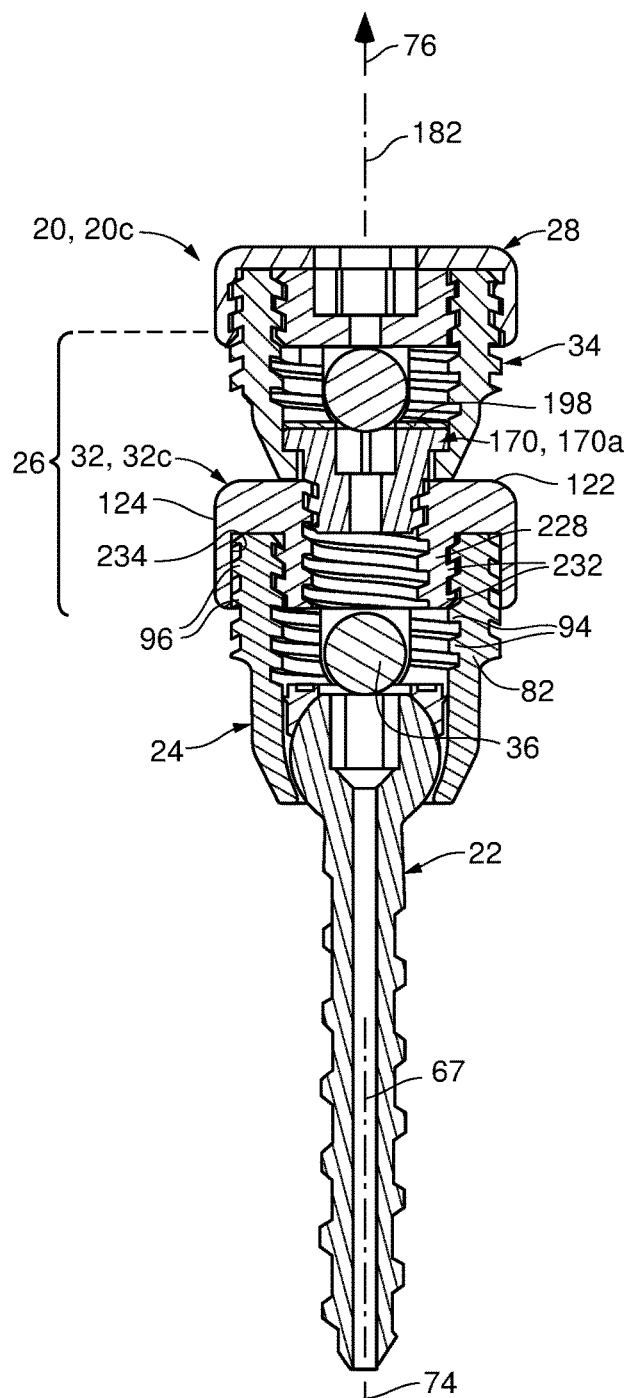
FIG. 6
FIG. 7

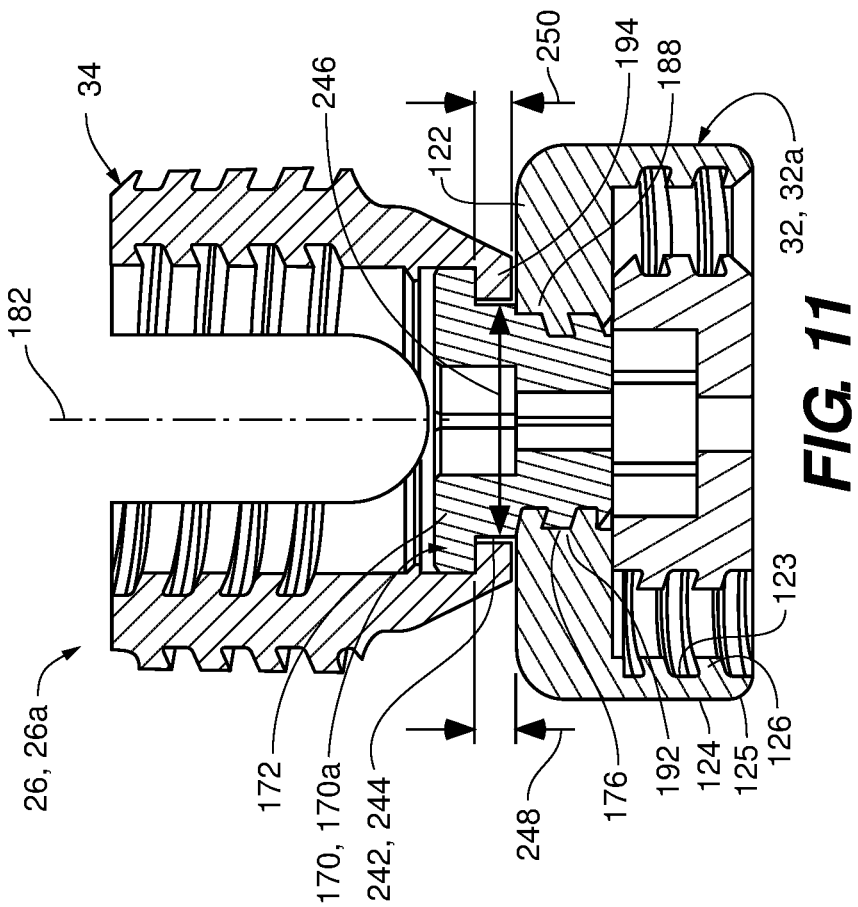
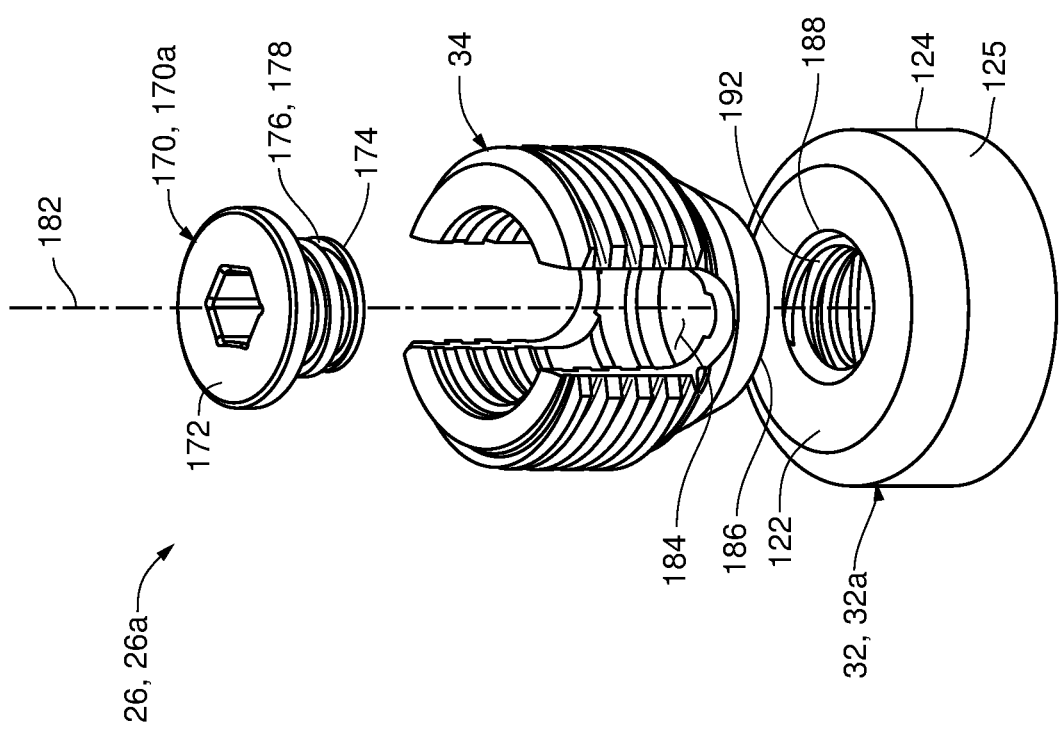

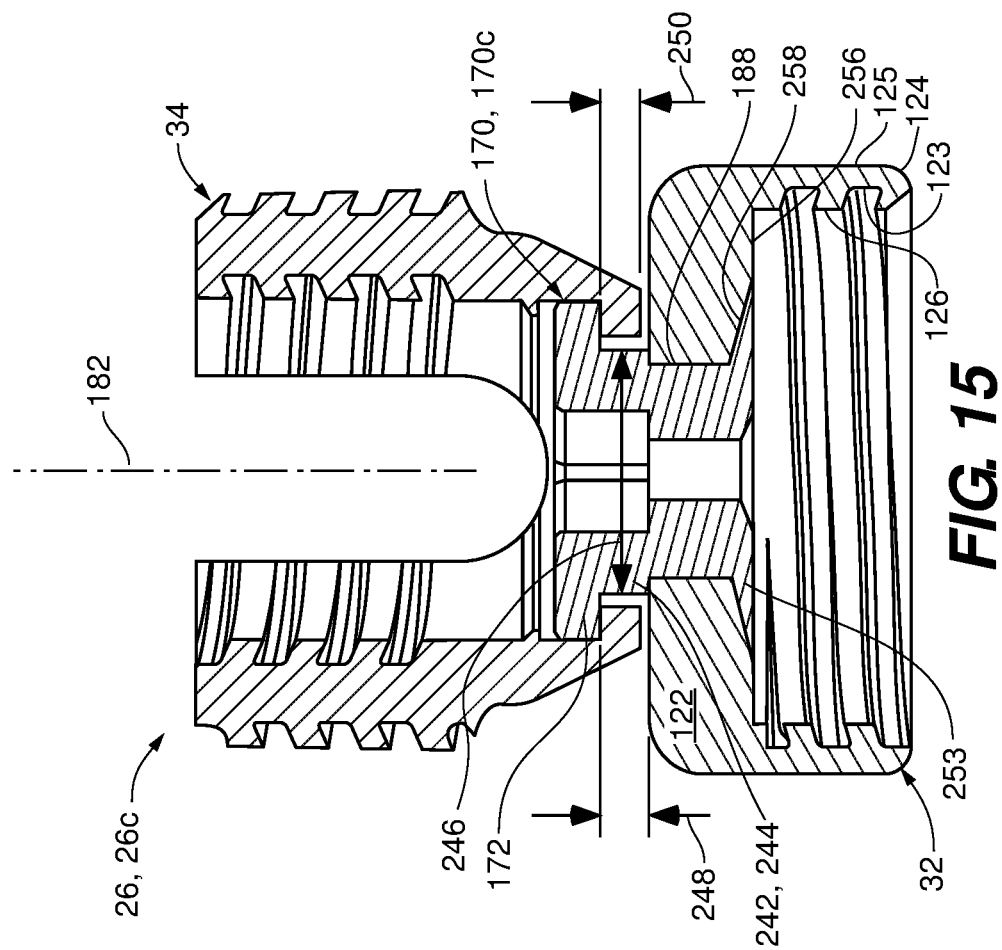
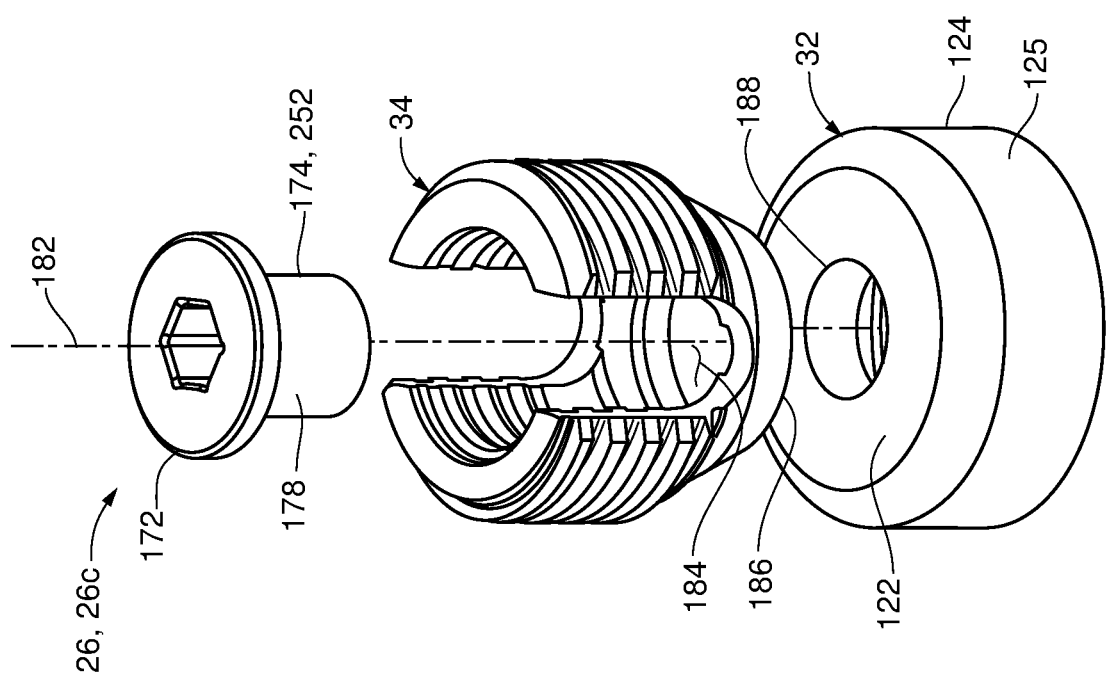

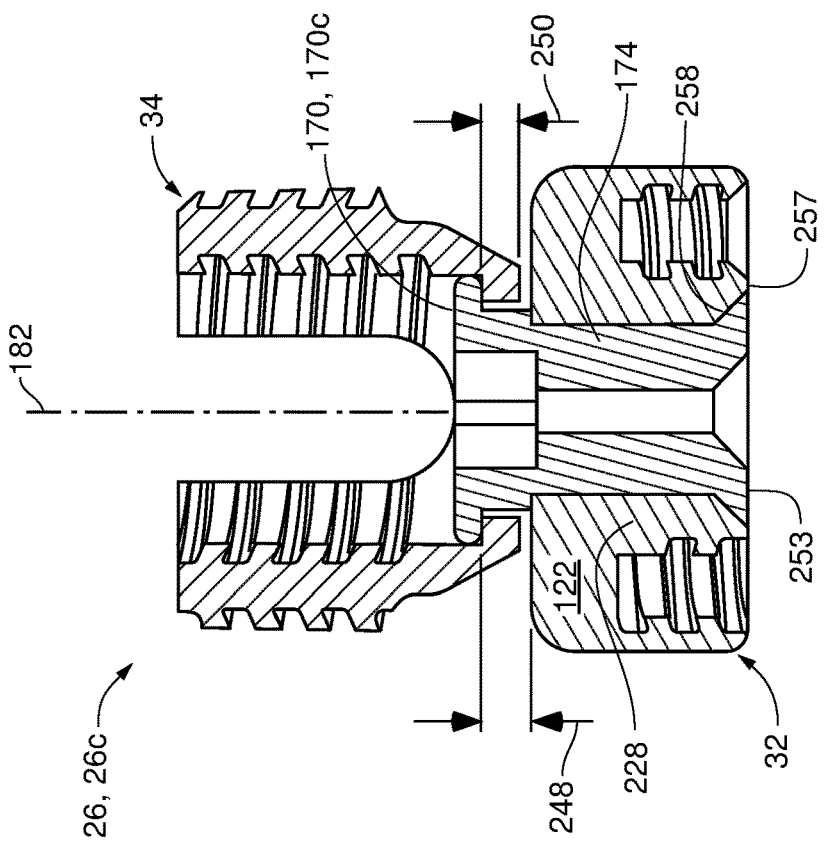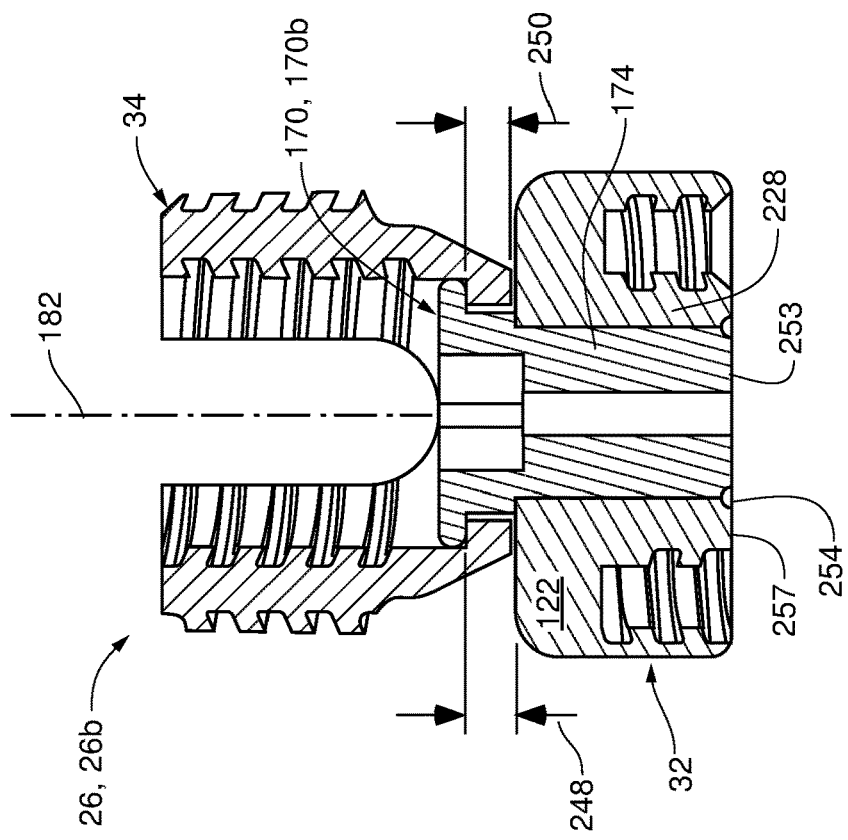

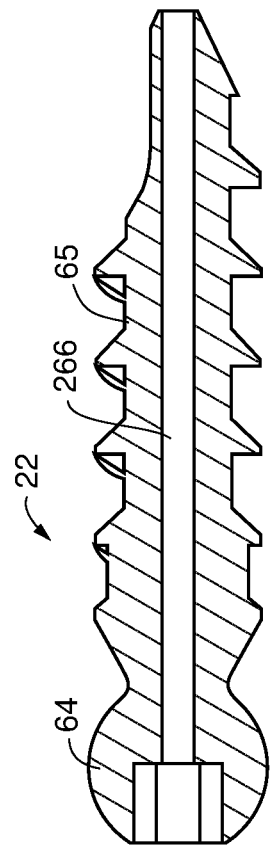
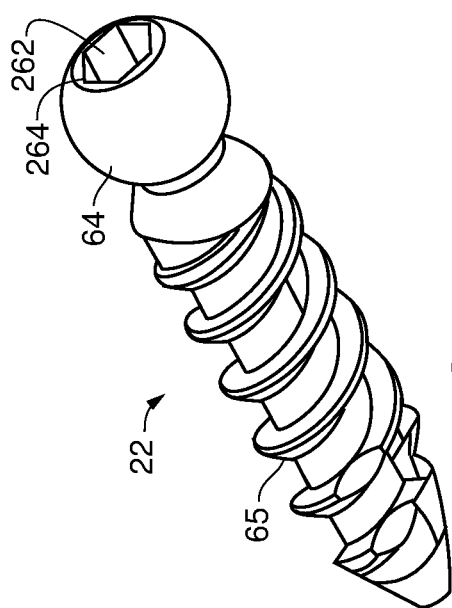
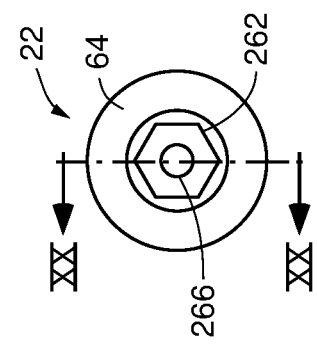

EXTENSION READY SPINAL SUPPORT SYSTEMS

RELATED APPLICATIONS

This patent application claims the benefit of U.S. Provisional Patent Application No. 62/500,820 filed on May 3, 2017, and U.S. Provisional Patent Application No. 62/500,719, also filed May 3, 2017, the disclosures of which are hereby incorporated by reference in their entirety.

FIELD OF THE DISCLOSURE

The present disclosure relates to spinal support systems and more particularly to a spinal support systems and methods that are extensible.

BACKGROUND OF THE DISCLOSURE

Implementation of various spinal surgical techniques often require the use of spinal support rods that are anchored to the vertebrae through the use of pedicle screws to provide stabilization of the spine during healing or correction. Examples include maintaining adjacent vertebrae stationary so that bone growth tissue can bridge the vertebrae in a spinal fusion process. Another example is the use of spinal support rods to apply a coercive force to the spine for corrective purposes (e.g., correction of scoliosis).

In some cases, surgery is later required to treat other vertebrae of the same patient. "Extension" systems have been developed which enable additional spinal support rods to be coupled to existing spinal rods or pedicle screws of the previous surgery, thereby reducing surgical trauma and recovery times. Such an extension system is found, for example, at U.S Patent Application Publication No. 2016/0242817 to Abbasi entitled "Spinal Rod Support Structure with Clamp," owned by the owner of the current application, the contents of which are incorporated by reference herein except for patent claims and express definitions contained therein.

The present application identifies shortcomings and limitations in the art of spinal rod extension systems and provides improvements to remedy such shortcomings and limitations.

SUMMARY OF THE DISCLOSURE

Various embodiments of the present disclosure provides an "extension ready" spinal support system that enables the extension to be accomplished with minimal disturbance to an existing spinal support structure to which the extension system is coupled. In some embodiments, existing connections between the existing spinal support rod and pedicle screws can remain intact while extension rod receptacles are mounted directly to the existing base rod receptacles. In some embodiments, the extension receptacle may be polyaxial with respect to the base receptacle. In other embodiments, the extension receptacle is provided with a low profile (i.e., shortened axial projection length from the base rod receptacle) relative to the polyaxial embodiment by eliminating polyaxial structure between the base receptacle and the extension receptacle and the additional axial lengths associated therewith and providing a monoaxial structure that rotates about but does not pitch relative to extension axis.

Conventional spinal rod extension systems exist where extension spinal support rod receptacles (also referred to as extension "tulips" in the parlance of the spinal support arts) can be mounted "piggyback" to an existing or "base" spinal support rod receptacle. However, conventional systems require that the connection between the base spinal support rod receptacle must be disturbed or modified. For example, in some systems, the set screw securing the base spinal rod to the base receptacle must be removed so that the extension receptacle can utilize the interior threads of the base receptacle. This releases the base spinal support rod from the base receptacle, thus requiring that the base spinal support rod be reset before the surgeon can proceed with implantation of the extension system. Often, the required structure that extends from the base receptacle is of undesirable axial length, causing concealment issues.

Another drawback of conventional rod receptacle arrangements is the separation or "splaying" of the tulip. When a conventional set screw is seated on the inside of a conventional tulip, forces are generated on the tulip wall portions that force the tulip wall sections away from each other. This separation of the tulip walls is referred to as "splaying."

Various embodiments of the disclosure alleviate one or more of these shortcomings and limitations. The disclosed embodiments enable extension of the spinal support structure without need for removing the tulips or pedicle screws of the already-implanted spinal support structure. Certain embodiments alleviate the need to remove the set screw from the interior threads of the base receptacle. As with conventional rod receptacles, the disclosed base rod receptacle includes interior threads to which a set screw is coupled for securing the base spinal support rod. In addition, the disclosed system further includes exterior threads to which an optional extension assembly can be mounted at a later time. By utilizing the exterior threads for mounting the extension system, the set screw that secures the base spinal support rod to the base rod receptacle does not have to be removed from the interior threads of the base rod receptacle. In this way, the base spinal support system can remain intact and undisturbed as the extension system is coupled thereto.

Other embodiments involve removal of the set screw from the base receptacle, but utilizes a reinforced, dual threaded or capped base that is stronger and more robust than standard set screw arrangements and prevents splaying of the tulip.

Structurally, a spinal support system is disclosed, comprising a first rod receptacle for mounting to a pedicle screw, the first rod receptacle having a first side wall that includes a first interior surface and a first exterior surface. The first side wall defines a first pair of diametrically opposed slots that extend axially along the first side wall and are open at a proximal end of the first rod receptacle, the first interior surface defining first interior threads. A first set screw includes threads configured to mate with the first interior threads of the first rod receptacle. The first exterior surface defines first exterior threads. An extension assembly including a base portion mounted to a second rod receptacle, the base portion including a mounting platform and a skirt portion that extends from the mounting platform, the skirt portion including interior threads for mating with the first exterior threads of the first rod receptacle, the second rod receptacle having a second side wall that includes a second interior surface and a second exterior surface. The second exterior surface of the second rod receptacle may include second exterior threads. The second side wall defines a second pair of diametrically opposed slots that extend axially along the second side wall and are open at a proximal end of the second rod receptacle, the second interior surface defining second interior threads. A second set screw includes threads configured to mate with the second interior threads of the second rod receptacle.

The extension assembly may include a pivot member that attaches the second rod receptacle to the base portion, the pivot member including a head portion and a shaft portion, the shaft portion including shaft threads formed on an exterior surface thereof, the shaft portion defining a pivot axis. In some embodiments, the second rod receptacle defines an opening at a distal end thereof, the opening sized to accommodate passage of the shaft portion of the pivot member. The mounting platform of the base portion may define a center hole for receiving the pivot member, and may include interior threads for mating with the external shaft threads. In some embodiments, the center hole is a through hole.

In some embodiments, the second rod receptacle includes an internal flange having an interior face, the head portion of the pivot member being dimensioned to register against the interior face of the internal flange to secure the second rod receptacle to the base portion. The head portion of the pivot member may be one of a flat head and a countersink head, and the interior face of the internal flange of the second rod receptacle may conforms to the head portion to enable selective monoaxial rotation about the pivot axis.

In some embodiments, a pedicle screw coupled to a distal end portion of the first rod receptacle. The pedicle screw and the first rod receptacle may be configured for polyaxial rotation of the first rod receptacle about a head of the pedicle screw. In some embodiments, a lock ring configured to engage a spinal support rod, the lock ring including a distal face that conforms to the pedicle screw and a proximal face that includes one or more malleable features for engaging the spinal support rod. The one or more malleable features may be plastically deformable. In some embodiments, the one or more malleable features includes a raised ridge. In some embodiments, the raised ridge is annular ring.

Some embodiments include a cap including a skirt portion having interior threads for mating with the second exterior threads of the second rod receptacle. In some embodiments, the skirt is not threaded, but instead provides a sliding fit over the exterior of the base rod receptacle to prevent splaying. An exterior surface of the skirt portion may define a plurality of flats, each of said plurality of flats being parallel to the pivot axis. In some embodiments, one or more of the first interior threads, the first exterior threads, the second interior threads, the second exterior threads, and the internal threads of the center hole define a canted cantilever profile. The canted cantilever profile may extend radially and in a distal direction.

In various embodiments of the disclosure, a spinal rod support system comprises an extension rod receptacle, a base portion including a mounting platform that defines a center hole accessible from a proximal face of the mounting platform, and means for coupling the extension rod receptacle to the base portion. In some embodiments, the means for coupling the extension rod receptacle to the base portion includes a pivot member threadably engaged with the center hole. In some embodiments, the means for coupling the extension rod receptacle to the base portion includes a pivot member swaged to the center hole. In some embodiments, the means for coupling the extension rod receptacle to the base portion includes a pivot member fused to the center hole. The pivot member may be welded to the center hole at a distal face of the base portion, for example, a distal face of the mounting platform.

The spinal support system may further comprise a base rod receptacle, and means for coupling the base portion to the base rod receptacle. In some embodiments, the base portion includes a skirt portion, and the means for coupling the base portion to the base rod receptacle includes threaded engagement of the skirt portion to the base rod receptacle. In some embodiments, the base portion includes a set screw portion that is unitary with and extends from a distal face of the mounting platform, and the means for coupling the base portion to the base rod receptacle includes threaded engagement of the set screw portion to the base rod receptacle. In some embodiments, the set screw portion and the base portion include mating threads that define canted cantilever profiles for the threaded engagement. The canted cantilever profiles may extend radially and in a distal direction. In some embodiments, the spinal support system comprises a base spinal support rod disposed in the base rod receptacle, the set screw portion being configured to clamp the base spinal support rod within the base rod receptacle. In some embodiments, the base portion includes a set screw portion that is unitary with and extends from a distal face of the mounting platform, and the means for coupling the base portion to the base rod receptacle includes threaded engagement of the set screw portion to the base rod receptacle. In some embodiments, the means for coupling the extension rod receptacle to the base portion enables only monoaxial rotation of the extension rod receptacle about a pivot axis.

In various embodiments of the disclosure, a method of fabricating an extension assembly for a spinal support system comprises: inserting a pivot member into a rod receptacle so that a shaft portion of the pivot member extends from a distal end of the rod receptacle; disposing the shaft portion in a center hole of a base portion so that an internal flange of the rod receptacle is captured between a head portion of the pivot member and the base portion so that an axial gap dimension defined between the head portion and the base member is greater than an axial thickness of the internal flange; and securing the pivot member to the base portion. In some embodiments, the step of disposing and the step of securing includes threadably engaging the shaft portion with the center hole. In some embodiments, the step of disposing includes registering a stop on the pivot member against the base portion to define the axial gap dimension. In some embodiments, the step of securing includes one of fusing and swaging the shaft member to the base portion.

BRIEF DESCRIPTION OF THE DRAWINGS

FIG. 1 is a perspective view of an extension ready base assembly according to an embodiment of the disclosure;

FIG. 2 is a sectional view of an extensible spinal support system in full assembly with the extension ready base assembly of FIG. 1 according an embodiment of the disclosure;

FIGS. 6 through 8 are sectional views of alternative extensible spinal support systems in full assembly with the extension ready base assembly of FIG. 1 according embodiments of the disclosure;

FIGS. 10 and 11 are sectional views depicting assembly of an extension sub-assembly having a threaded pivot member according to an embodiment of the disclosure;

FIGS. 14 and 15 are sectional views depicting assembly of an extension sub-assembly having a riveted pivot member according to an embodiment of the disclosure;

FIGS. 16 and 17 are sectional views of extension sub-assemblies with base portions that have integral set screw portions according to an embodiment of the disclosure;

FIG. 18 is a perspective view of the pedicle screw of FIGS. 1 and 2 according to an embodiment of the disclosure;

FIG. 19 is a top axial view of the pedicle screw of FIG. 18 according to an embodiment of the disclosure;

FIG. 20 is a sectional view of the pedicle screw at plane XX-XX of FIG. 18 according to an embodiment of the disclosure;

DETAILED DESCRIPTION OF THE FIGURES

Figure 1A:
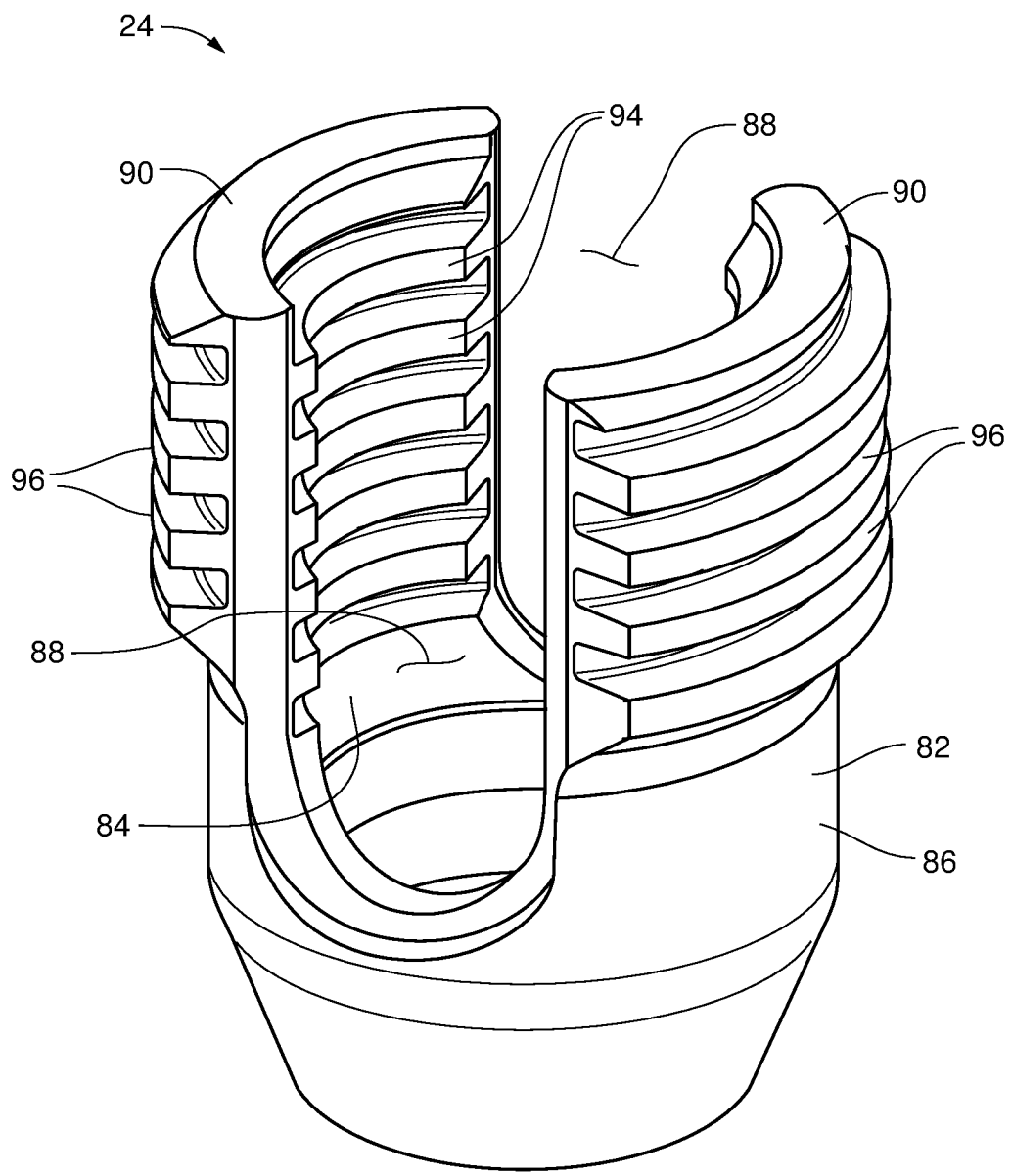
FIG. 1A is an upper perspective view of a base rod receptacle of FIG. 1 in isolation according to an embodiment of the disclosure.

Referring to FIGS. 1 through 5, an extensible spinal support system 20 is depicted according to an embodiment of the disclosure. The extensible spinal support system 20 as depicted includes an extension ready base assembly 21 including a pedicle screw 22, a first or base rod receptacle 24, a first or base set screw 42, and a first spinal support rod 36 (FIG. 1). The extensible spinal support system 20 further includes an extension subassembly 26 and a cap 28 (FIG. 2). The extension subassembly 26 includes a base portion 32 and a second or extension rod receptacle 34. The base rod receptacle 24 is configured to receive the first or base spinal support rod 36, and the extension rod receptacle 34 is configured to receive a second or extension spinal support rod 38. In the depicted embodiments, the base spinal support rod 36 is retained within the base rod receptacle 24 with the base set screw 42. Likewise, for the extensible spinal support system 20, the extension spinal support rod 38 is retained within the extension rod receptacle 34 with a second or extension set screw 44.

The pedicle screw 22 includes a head portion 64 and a threaded shaft portion 65 centered about a central axis 67. The pedicle screw 22 extends from a distal end 62 of the base rod receptacle 24, the head portion 64 being captured within the distal end 62 of the base rod receptacle 24. In some embodiments, a lock ring 66 is disposed interstitially between the base spinal support rod 36 and the head portion 64 of the pedicle screw 22. In the depicted embodiment, the head portion 64 of the pedicle screw 22 defines a spherical surface portion 68, with the base rod receptacle 24 including a complementary mating surface 72 that engages and conforms to the spherical surface portion 68 of the head portion 64 of the pedicle screw 22.

Functionally, the spherical surface portion 68 of the head portion 64 of the pedicle screw 22 and conforming mating surface 72 of the base rod receptacle 24 enable the base rod receptacle 24 to pitch about the head portion 64 of the pedicle screw 22 relative to the central axis 67, and to rotate about the head portion 64 in any of the pitched orientations. By this arrangement, the pedicle screw 22 and the base rod receptacle 24 are configured for polyaxial rotation of the base rod receptacle 24 about the head portion 64 of the pedicle screw 22.

Herein, "proximal" refers to a direction 76 that is toward a surgeon during operation or implantation and away from a bone or patient. "Distal" refers to a direction 74 that is away from the surgeon during operation or implantation and toward the bone or patient to which the extensible spinal support system 20 is implanted (i.e., a direction opposite the distal direction 76).

The base rod receptacle 24 includes a side wall 82 having an interior surface 84 and an exterior surface 86. A pair of diametrically oppose slots 88 are defined on the side wall 82, the slots 88 extending axially along the side wall 82 and being open at a proximal end 92 of the base rod receptacle 24. By formation of the diametrically opposed slots 88, the side wall 82 defines diametrically opposed wall segments 90 on opposing sides of the diametrically opposed slots 88. The interior surface 84 extends axially along the side wall 82 and includes interior threads 94 formed thereon. The exterior surface 86 also extends axially and includes exterior threads 96 formed thereon. The base portion 32 of the extension subassembly 26 includes a mounting platform 122 and a skirt portion 124 that extends from the mounting platform 122 in the distal direction 74. The skirt portion 124 includes an interior surface 123 and an exterior surface 125.

Figure 5:
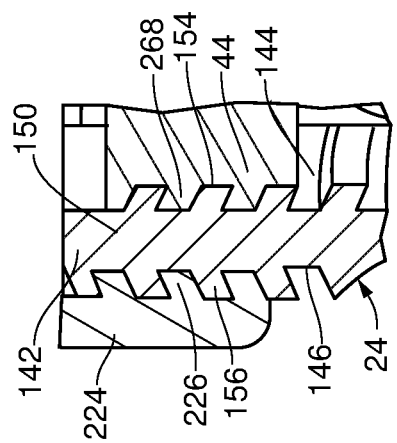
FIG. 5 is an enlarged, partial sectional view of a threaded wall portion of an extension rod receptacle of the assembly of FIG. 2 according to an embodiment of the disclosure.
Figure 4:
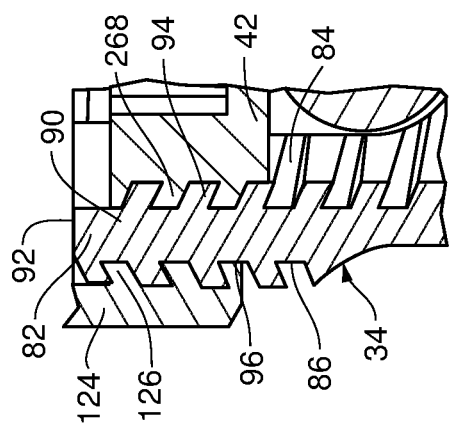
FIG. 4 is an enlarged, partial sectional view of a threaded wall portion of a base rod receptacle of the assembly of FIG. 2 according to an embodiment of the disclosure.
Figure 3:
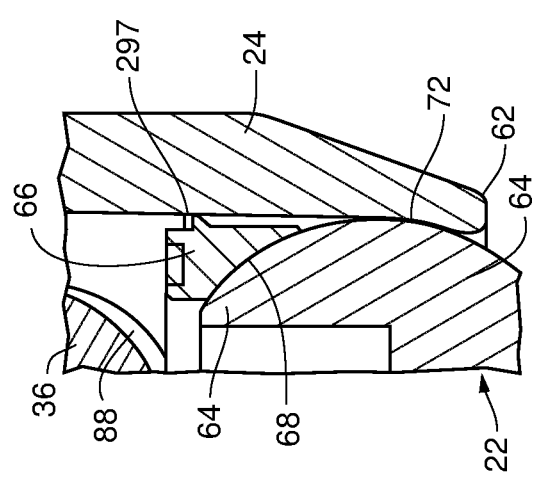
FIG. 3 is an enlarged, partial sectional view of a lock ring in the assembly of FIG. 2 according to an embodiment of the disclosure.

The extension rod receptacle 34 includes a side wall 142 having an interior surface 144 and an exterior surface 146. A pair of diametrically opposed slots 148 are defined on the side wall 142, the slots 148 extending axially along the side wall 142 and being open at a proximal end 152 of the extension rod receptacle 34. By formation of the diametrically opposed slots 148, the side wall 142 defines diametrically opposed wall segments 150 on opposing sides of the diametrically opposed slots 148. The interior surface 144 extends axially along the side wall 142 and includes interior threads 154 formed thereon (FIG. 5). The exterior surface 146 also extends axially and includes exterior threads 156 formed thereon.

In the depicted embodiment, the extension subassembly 26 includes a pivot member 170 that attaches the extension rod receptacle 34 to the base portion 32, the pivot member 170 including a head portion 172 and a shaft portion 174 and defining a through passage 175. The shaft portion defines a pivot axis 182. The extension rod receptacle 34 defines an opening 184 at a distal end 186 thereof. The opening 184 is sized to accommodate passage of the shaft portion 174 of the pivot member 170.

In the depicted embodiment, the mounting platform 122 of the base portion 32 defines a center hole 188 for receiving the pivot member 170. The extension rod receptacle 34 may include an internal flange 194 having an interior face 196, the head portion 172 of the pivot member 170 being dimensioned to extend radially over the interior face 196 of the internal flange 194 to loosely secure the extension rod receptacle 34 to the base portion 32. The head portion 172 of the pivot member 170 may be one of several head styles available to the artisan, for example a flat head (depicted), a socket head, a countersink head, or a spherical head. The interior face 196 of the internal flange 194 may be configured to conform to the head portion 172. In some embodiments, a collet 198 is disposed interstitially between the extension spinal support rod 38 and the head portion 172. The collet 198 may be a disc spring (depicted), lock washer, or other that exerts a bias force parallel to the pivot axis 182 when compressed between the support rod 38 and the head portion 172. The cap 28 includes a top portion 222 and a skirt portion 224 that extends from the mounting platform 222. The skirt portion 224 includes interior threads 226 for mating with the exterior threads 156 of the extension rod receptacle 34.

In operation, the pedicle screw 22 is inserted into the base rod receptacle 24 so that the head portion 64 of the pedicle screw 22 can be registered against the mating surface 72 of the base rod receptacle 24. The pedicle screw 22 is set into the bone of a vertebrae. The lock ring 66, if utilized, is disposed within the base rod receptacle 24 and arranged for contact with the head portion 64 of the pedicle screw 22. The base rod receptacle 24 is arranged in a desired orientation on the head portion 64 of the pedicle screw 22 and the base spinal support rod 36 disposed in the base rod receptacle 24. The lock ring 66 is thereby disposed between the base spinal support rod 36 and the head portion 64 of the pedicle screw 22. The base set screw 42 is threadably engaged with the interior threads 94 of the side wall 82 and tightened so that the base spinal support rod 36 is clamped between the base set screw 42 and the lock ring 66 (if utilized) or, alternatively, the head portion 64 of the pedicle screw 22. The tightening of the base set screw 42 also seats the head portion 64 of the pedicle screw 22 against the mating surface 72 of the base rod receptacle 24 to secure the base rod receptacle 24 in the desired orientation relative to the head portion 64.

Referring to FIGS. 6 and 7 and again to FIG. 2, extensible spinal support systems 20 having alternative embodiments for the base portion 32 are presented according to embodiments of the disclosure. In FIGS. 2, 6, and 7, the extensible spinal support systems and their associated base portions are referred to collectively and generically by reference characters 20 and 32, respectively, and specifically by the reference characters 20 and 32 followed by a letter suffix (e.g., extensible spinal support system 20a and the associated base portion 32a). Several components and attributes are common to all extensible spinal support systems 20, which are indicated with same numbered reference characters.

For the extensible spinal support system 20a (FIG. 2), the base portion 32a and the base set screw 42 are separate components that are installed independently of each other. For the extensible spinal support systems 20a and 20b, the skirt portion 124 includes interior threads 126 for mating with the exterior threads 96 of the base rod receptacle 24. For the extensible support system 20b (FIG. 6), the base portion 32b additionally includes a set screw portion 228 that is integral therewith, the set screw portion 228 having external threads 232 that mate with the interior threads 94 of the side wall 82 of the base rod receptacle 24. Accordingly, for the extensible spinal support system 20b, the external threads 232 of the set screw portion 228 and the interior threads 226 of the skirt portion 124 of the base portion 32b are threaded simultaneously. For the extensible spinal support system 20c (FIG. 7), the base portion 32c also includes the set screw portion 228 that is integral therewith, and having external threads 232 that mate with the interior threads 94 of the side wall 82 of the base rod receptacle 24. However, for the extensible spinal support system 20c, an inner surface 234 the skirt portion 124 is smooth (does not include interior threads), such that the skirt portion 124 rotates about and slides over but does not threadably engage the exterior threads 96 of the base rod receptacle 24. Accordingly, the base portion 32c mates only with the interior threads 94 of the side wall 82.

By integrating the set screw portion 228 with the mounting platform 122 as in subassemblies 26b and 26c, and skirt portion 124 the structural integrity of the extensible spinal support system 20 is enhanced. For example, lateral forces applied to the extensible spinal support system 20 will incur greater resistance because the integrated set screw portion 228 is unitary with the mounting platform 122, establishing a shear stress at the junction of the integrated set screw portion 228 and the mounting platform 122 that provides additional resistance to deformation relative to the extension subassemblies 26 of FIGS. 10 through 15.

Functionally, each of the extensible support systems 20 provide a unique advantage. Extensible spinal support system 20a enables mounting of the extension assembly 26 without disturbing the base set screw 42, eliminating the need to reset the base spinal support rod 36. The extensible spinal support system 20a may find application where disturbance of the base spinal support system is not necessary or is ill advised. Extensible spinal support system 20b provides a dual threaded arrangement that enhances structural integrity of the extension assembly 26 to the base rod receptacle 24. Such enhancement of the structural integrity may be advantageous for high torque and high stress applications, such as scoliosis correction. Extensible spinal support system 20c also includes the integrated set screw portion 228 and attendant benefit while the smooth, sliding fit of the skirt portion 124 enables easier installation where the dual threaded arrangement of the extensible spinal support system 20b may be unnecessary or difficult. The sliding fit of the skirt portion 124 for the extensible spinal support system 20c effectively captures the side walls 82 of the base rod receptacle 24 to limit splaying. The extensible spinal support system 20c can also be configured for retrofitting with tulips of other spinal support systems that are not extension ready.

Figure 8:
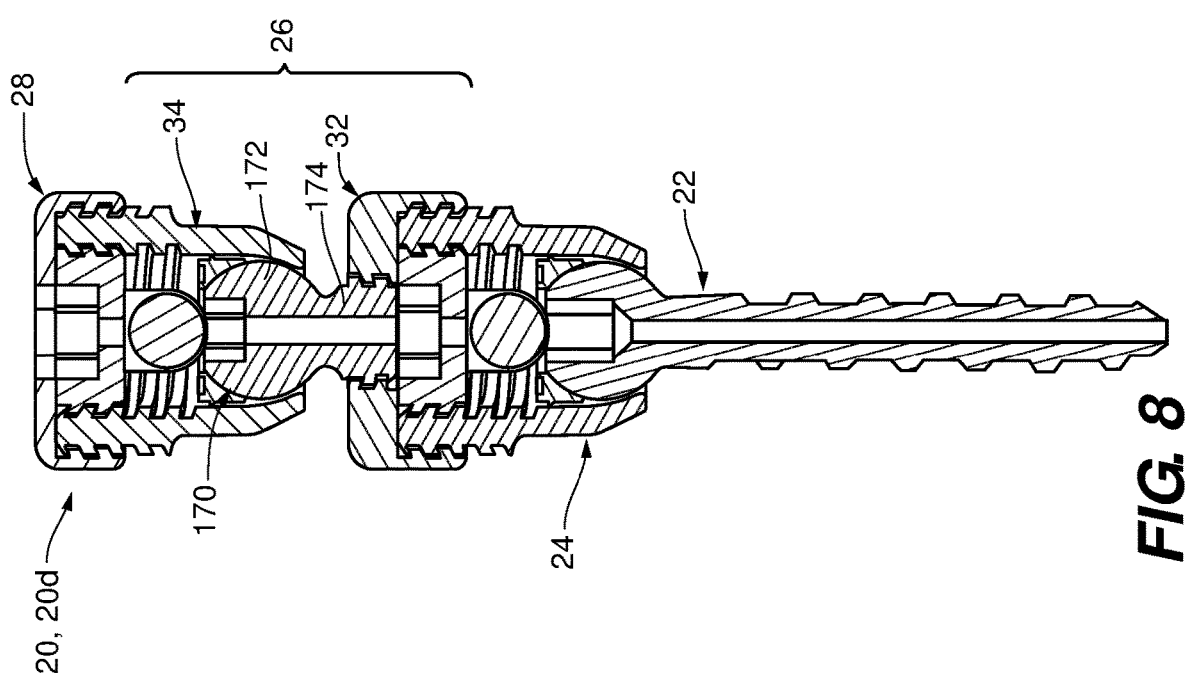
Figure 13:
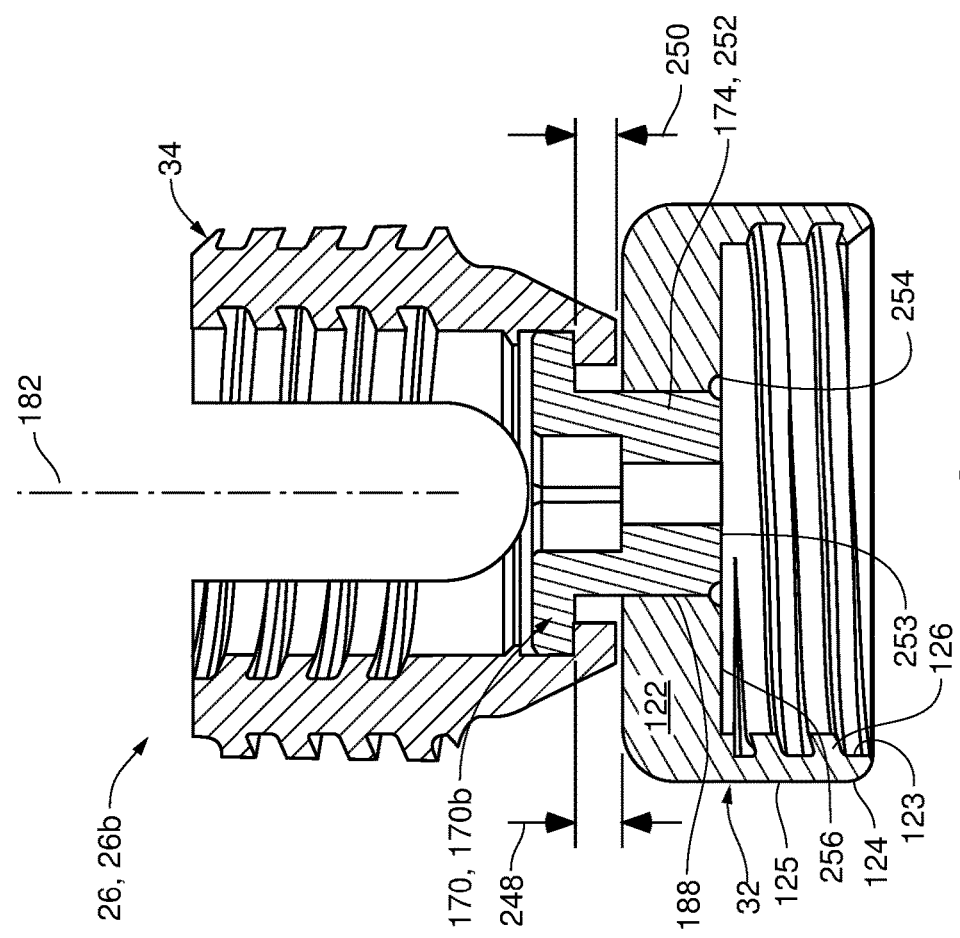
FIGS. 12 and 13 are sectional views depicting assembly of an extension sub-assembly having a welded pivot member according to an embodiment of the disclosure.
Figure 12:
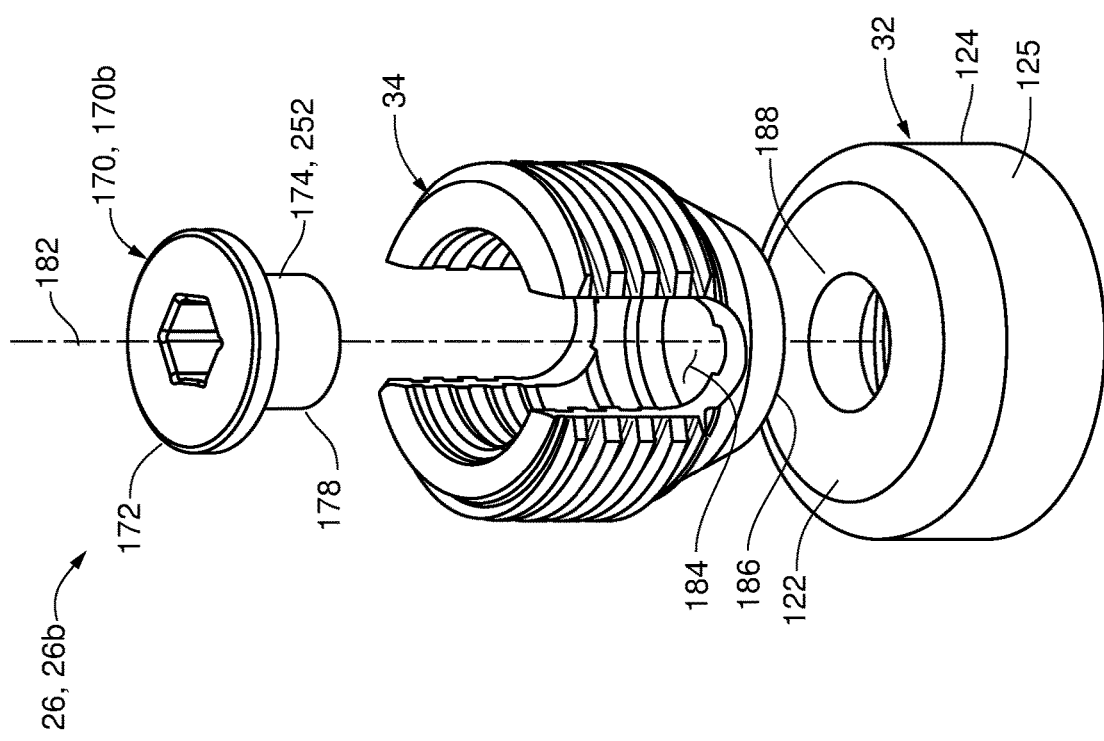

Referring to FIG. 8, an extensible spinal support system 20d is depicted according to an embodiment of the disclosure. As depicted the extensible spinal support system 20d includes many of the same components and attributes as the extensible spinal support system 20a, which are indicated with same numbered referenced characters. While components and attributes of the extensible spinal support system 20a are presented in the extensible spinal support system 20d, such components and attributes are not limiting. That is, the extensible spinal support system 20d may implement various aspects of the extensible spinal support systems 20b and 20c as well.

For the extensible spinal support system 20d, the head portion 172 of the pivot member 170d is spherical, and the extension rod receptacle 34 is configured as discussed above for the base rod receptacle 24. By this arrangement, the pivot member 170 and the extension rod receptacle 34 are configured for polyaxial rotation of the extension rod receptacle 34 about the head portion 172 of the pivot member 170.

Figure 9:
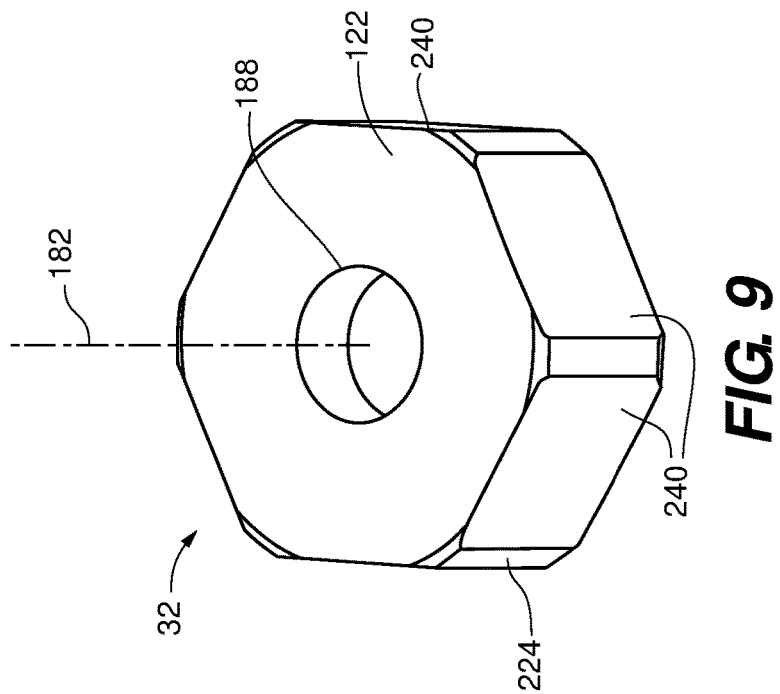
FIG. 9 is a perspective view of a platform of an extensible spinal support system with exterior wrench flats according to an embodiment of the disclosure.

Referring to FIG. 9, the skirt portion 124 of the base portion 34 is depicted with flats 240 according to an embodiment of the disclosure. The flats 240 are parallel to the pivot axis 182 and may be implemented with any of the depicted or contemplated embodiments. The embodiment of FIG. 9 depicts a total of six flats 240 as a non-limiting example. In some embodiments the number of flats 240 is in a range of six to twelve inclusive. In some embodiments, the skirt portion 124 defines two flats 240 that are diametrically opposed. In some embodiments, the skirt portion 124 defines four flats 240 that are distributed as two diametrically opposed pairs that are rotationally offset at 90 degrees with respect to each other.

Referring to FIGS. 10 through 17, assembly of various extension subassemblies 26 are depicted according to embodiments of the disclosure. In FIGS. 10 through 17, the extension subassemblies and their associated pivot members are referred to collectively and generically by reference characters 26 and 170, respectively, and specifically by the reference characters 26 and 170 followed by a letter suffix (e.g., extension subassembly 26a and the associated pivot member 170a). Several components and attributes are common to all extension subassemblies 26, which are indicated with same numbered reference characters.

For the extension subassembly 26a (FIGS. 10 and 11), the pivot member 170a defines exterior shaft threads 176 formed on an exterior surface 178 of the shaft portion 174. The center hole 188 of the mounting platform 122 includes internal threads 192 for mating with the exterior shaft threads 176. In some embodiments, the pivot member 170a includes a stop 242, such as a shoulder 244 having a diameter 246 that is greater than the diameter of the exterior shaft threads 176. The stop 242 cooperates with the head portion 172 to define an axial gap dimension 248 that is greater than an axial thickness 250 of the internal flange 194.

In assembly, the pivot member 170a is inserted through the extension rod receptacle 34 and into the opening 184 so that the shaft portion 174 extends from the distal end 186 of the extension rod receptacle 34 and the head portion 172 of the pivot member 170a is within the extension rod receptacle 34. The shaft portion 174 of the pivot member 170a and the center hole 188 of the mounting platform 122 of the base portion 32a are then aligned and the exterior shaft threads 176 of the shaft portion 174 threaded into the internal threads 192 of the center hole 188. In some embodiments, the pivot member 170a is threaded into the center hole 188 until the stop 242 is firmly seated against the platform 122 over the mouth of the center hole 188 to define the axial gap dimension 248. Alternatively, the pivot member 170a may otherwise engage the base portion 32a in a manner that causes the pivot member 170a to stop within the center hole 188; for example, the threads 176 may cease at a point on the pivot shaft 174 that provides the desired axial gap dimension 248. Having secured the pivot member 170a to the mounting platform 122, the extension rod receptacle 34 is coupled to the base portion 32.

For the extension subassembly 26b (FIGS. 12 and 13), the shaft portion 174 of the pivot member 170b is a right cylinder 252, defining a smooth exterior surface 178. The center hole 188 of the mounting platform 122 is also right cylindrical, and may be dimensioned to provide a close sliding fit with the shaft portion 174. In some embodiments, the pivot member 170a includes a stop (not depicted) akin to pivot member 170a.

In assembly, the pivot member 170b is inserted through the extension rod receptacle 34 and into the opening 184 so that the shaft portion 174 extends from the distal end 186 of the extension rod receptacle 34 and the head portion 172 of the pivot member 170b is within the extension rod receptacle 34. The shaft portion 174 of the pivot member 170b and the center hole 188 of the mounting platform 122 of the base portion 32 are then aligned and the shaft portion 174 positioned within the center hole 188 to so that the axial gap dimension 248 is defined between the head portion 172 and the mounting platform 122. In some embodiments, the pivot member 170a is threaded into the center hole 188 until the stop 242 is firmly seated against the platform 122 over the mouth of the center hole 188, thereby defining the axial gap dimension 248. In some embodiments, the length of the shaft portion 174 is dimensioned to provide the desired axial gap dimension 248 when a distal end 253 of the shaft portion 174 is flush with a distal face 256 of the platform 122.

With the pivot member 170b positioned in the center hole 188 to define the axial gap dimension 248 greater than the axial thickness 250 of the internal flange 194, the pivot member 170b is secured to the platform 122. In the depicted embodiment, the distal end 253 of the pivot member 170b is welded to the distal face 256 of the mounting platform 122 to form a weld 254 at the perimeter of the center hole 188. The weld 254 may be continuous, a stitch weld, or a tack weld. The welding operation may be performed with welding techniques available to the artisan, including but not limited to electron beam welding. Alternatively, instead of welding, the pivot member 170b may be secured by other bonding or fusion techniques, such as brazing, soldering, or gluing. Upon securing the pivot member 170b to the base portion 32, the internal flange 294 of the extension rod receptacle 34, being captured between the head portion 172 and the mounting platform 122, is coupled to the base portion 32.

For the extension subassembly 26c (FIGS. 12 and 13), the shaft portion 174 of the pivot member 170c is also the right cylinder 252, defining the smooth exterior surface 178. The center hole 188 of the mounting platform 122 is also right cylindrical, and may be dimensioned to provide a close sliding fit with the shaft portion 174. Similar to the pivot member 170a, the pivot member 170c may include the stop 242 such as the shoulder 244 with diameter 246, the diameter 246 being greater than the diameter of the center hole 188. As with the subassembly 26a, the stop 242 of the subassembly 26c cooperates with the head portion 172 to define an axial gap dimension 248 that is greater than an axial thickness 250 of the internal flange 194. The distal face 256 of the mounting platform 122 may define a recessed lead in 258 that surrounds the center hole 188.

In assembly, the pivot member 170c is inserted through the extension rod receptacle 34 and into the opening 184 so that the shaft portion 174 extends from the distal end 186 of the extension rod receptacle 34 and the head portion 172 of the pivot member 170c is within the extension rod receptacle 34. The shaft portion 174 of the pivot member 170c and the center hole 188 of the mounting platform 122 of the base portion 32 are then aligned and the shaft portion 174 positioned within the center hole 188 so that the axial gap dimension 248 is defined between the head portion 172 and the mounting platform 122. In some embodiments, the pivot member 170c is inserted into the center hole 188 until the stop 242 registers against the platform 122 over the mouth of the center hole 188, thereby defining the axial gap dimension 248. In some embodiments, the length of the shaft portion 174 is dimensioned to provide the desired axial gap dimension 248 when the distal end 253 is flush with the distal face 256 of the platform 122.

With the pivot member 170c positioned in the center hole 188 to define the axial gap dimension 248 greater than the axial thickness 250 of the internal flange 194, the pivot member 170c is secured to the platform 122 by a swaging process. The swaging process deforms the distal end 253 of the shaft portion 174 into the recessed lead in 258. In this way, the mounting platform 122 is swaged between the stop 242 and the deformed distal end 253 of the pivot member 170c, akin to a rivet. The internal flange 294 is captured between the head portion 172 of the pivot member 170c and the mounting platform 122 of the base portion 32, thereby coupling the extension rod receptacle 34 to the base portion 32.

The depictions of FIGS. 10 through 15 present base portions 32 akin to base portion 32a, i.e., without an integral set screw portion. However, the assembly techniques for the subassemblies 26 described above are readily implemented for base portions 32 that include the set screw portion 228 integral therewith, akin to base portions 32b and 32c. The embodiments of FIGS. 6 and 7 depict the threaded pivot member 170a in combination with the integral set screw portion 228. The embodiments of FIGS. 16 and 17 depict the pivot members 170b and 170c with longer shaft portions 174 having distal ends 253 that reach the distal faces 257 of the integral set screw portions 228. The weld 254 (FIG. 16) and the recessed lead in 258 (FIG. 17) are formed on the distal faces 257 of the integral set screw portion 228. Accordingly, the subassemblies 26 may be fabricated with any of the base portions 32 described and depicted herein.

For the various subassemblies 26, because the axial gap dimension 248 is greater than the axial thickness 250 of the internal flange 194, monoaxial rotation of the extension rod receptacle 34 about the pivot axis 182 is achieved. That is, the internal flange 194, though effectively captured between the head portion 172 of the pivot member 170 and the base portion 32 of the extension subassembly 26, can be rotated about the pivot axis 182. In the depicted embodiment, movement of the of the extension rod receptacle 34 relative to the base portion 32 is effectively limited to rotation about the pivot axis 182, i.e., a "monoaxial" rotation.

For the subassemblies 26a and 26b, because of the exterior threads 96 on the side wall 82 of the base rod receptacle 24, the extension rod receptacle 34 can be mounted to the base rod receptacle 24. That is, the extension subassemblies 26a and 26b can be mounted directly to the exterior threads 96 of the base rod receptacle 24. For the subassembly 26c, the extension rod receptacle 24 can be mounted to the interior threads of the base rod receptacle 24, without need for exterior threads on the sidewall 82. Accordingly, because of the subassemblies 26, the base rod receptacle 24 is referred to as "extension ready."

For the pre-assembled extension subassembly 26a, the base portion 32 is aligned with the base rod receptacle 24 and the interior threads 126 of the skirt portion 124 of the base portion 32 threaded over the exterior threads 96 of the base rod receptacle 24. For the pre-assembled extension subassembly 26b, the base portion 32 is aligned with the base rod receptacle 24 and both the interior threads 126 of the skirt portion 124 and the exterior threads external threads 232 of the set screw portion 228 are threadably engage with the exterior threads 96 of the base rod receptacle 24 and the internal threads 192 of the center hole 188, respectively.

Because the pivot member 170 is in fixed relationship with the base portion 32, the base portion 32 may be drawn tight against the proximal end 92 of the base rod receptacle 24 by with a driver inserted in the socket of the pivot member 170. For monoaxial embodiments, the extension rod receptacle 34 may be rotated to a desired angular orientation about the pivot axis 182. The extension spinal support rod 38 is inserted into the extension rod receptacle 34, extending laterally through the diametrically opposed slots 148. The extension set screw 44 or, alternatively, the set screw portion 228, is threadably engaged with the interior threads 154 of the side wall 142 and tightened. When the set screw 44 is tightened against the extension spinal support rod 38, the extension rod receptacle 34 is drawn in the proximal direction (upward in FIG. 2) so that the internal flange 194 is drawn tight against the head portion 172, thereby locking the extension rod receptacle 34 in place and in a fixed rotational orientation relative to the head portion 172.

In some embodiments, in the absence of the extension subassembly 26, the cap 28 can be mounted to the exterior threads 96 of the base rod receptacle 24. Functionally, this arrangement provides support against outward lateral deflections (splaying) of the wall segments 90 would otherwise be provided by the skirt portion 124 of the mounting platform 122 of the extension subassembly 26a. Other caps can be implemented with either the base rod receptacle 24 or the extension rod receptacle 34, such as disclosed at U.S. patent application Ser. No. 15/970,429, entitled "Reinforcement Caps for Spinal Support Systems", filed on even date and owned by the owner of the present application, the disclosure of which is hereby incorporated by reference herein.

Similar to the extensible spinal support system 20a of FIG. 2, the extensible spinal support systems 20b and 20c of FIGS. 6 and 7 may be mounted to a previously implanted extension ready base assembly without need for removing or otherwise releasing the base spinal support rod 36. The base portions 32b and 32c of the extension subassemblies 26b and 26c may be mounted to the extension ready base assembly 21 of FIG. 1 instead of the set screw 42, the base portions 32b and 32c serving as a cap for securing the base spinal rod 36 to the base rod receptacle 24. The extension rod receptacle 34 can later be mounted directly to the center hole 188 of the mounting platform 122 of the base portion 32b with the pivot member 170a, thereby leaving the arrangement of the base rod receptacle 24 the base portions 32b, 32c and the base spinal support rod 36 intact. Accordingly, the base rod receptacle 24 in combination with the base portions 32b or 32c is also referred to as "extension ready." In such an embodiment, the extension subassemblies 26b and 26c are not pre-assembled, but instead assembled on the existing base portion 32b, 32c, being built up from the mounting platform 122 as described above.

Referring to FIGS. 18 through 20, the pedicle screw 22 is depicted in isolation in an embodiment of the disclosure. In addition to the components and attributes discussed above, the pedicle screw 22 may define a socket 262 in the head portion 64, accessible from a proximal end 264 of the pedicle screw 22. The threaded shaft portion 65 may be double threaded as depicted. In some embodiments, a center passage 266 extends through the head portion 64 and threaded shaft portion 65. In the depicted embodiment, the socket 262 is hexagonal, but other geometries, such as a square, rectangle, cross, or star pattern may be utilized.

Functionally, the socket 262 accommodates driving of the pedicle screw 22 with an appropriate mating wrench (e.g., hexagonal wrench for the depicted embodiment, or a square bit, rectangular bit, cross (PHILLIPS) bit, or star (TORR®) bit as appropriate). The center passage 266 may be sized, for example, to accommodate sliding passage of a Kirschner wire or a larger diameter rod.

Figure 21:
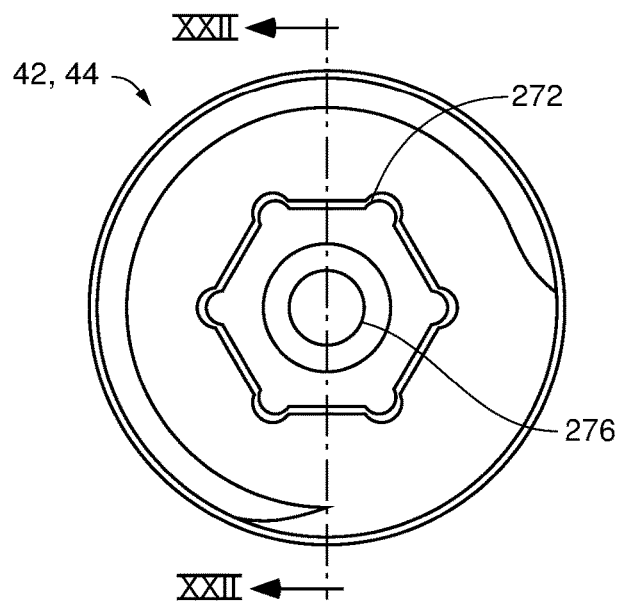
FIG. 21 is a top axial view of a set screw according to an embodiment of the disclosure.
Figure 22:
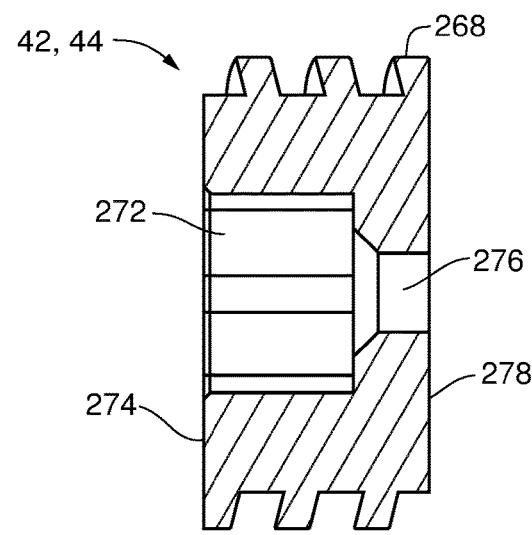
FIG. 22 is a section view of the set screw XXII-XXII of FIG. 21 at plane according to an embodiment of the disclosure.
Figure 23:
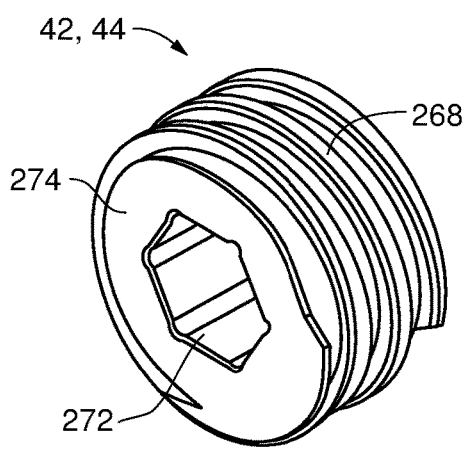
FIG. 23 is a perspective view of the set screw of FIG. 21 according to an embodiment of the disclosure.

Referring to FIGS. 21 through 23, the base or extension set screw 42, 44 is depicted in isolation in an embodiment of the disclosure. In the depicted embodiments, the base and extension set screws 42 and 44 are identical and are referred to collectively and generically as the "set screw 42, 44". The set screw 42, 44 includes exterior threads 268 that mate with the interior threads 94, 154 of the base or extension rod receptacle 24, 34. The set screw 42, 44 may define a socket 272, accessible from a proximal end 274 of the set screw 42, 44. In some embodiments, a center passage 276 extends from the socket 272 through a distal end 278 of the set screw 42, 44. In the depicted embodiment, the socket 272 is hexagonal, but other geometries, such as a square, rectangle, cross, or star pattern may be utilized.

Functionally, the socket 272 accommodates driving of the set screw 42, 44 with an appropriate mating wrench (e.g., hexagonal wrench for the depicted embodiment, or a square bit, rectangular bit, cross (PHILLIPS) bit, or star (TORR®) bit as appropriate). The center passage 276 may be sized, for example, to accommodate sliding passage of a Kirschner wire or larger diameter rod.

Figure 24:
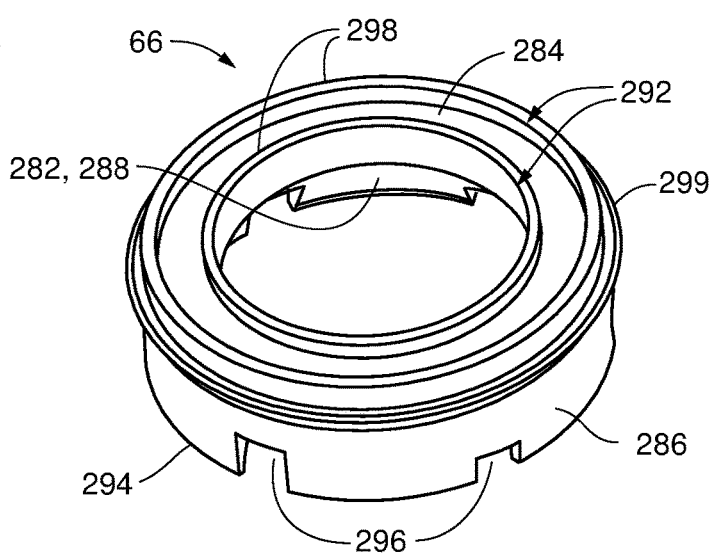
FIG. 24 is a perspective view of a lock ring according to an embodiment of the disclosure.

Referring to FIG. 24, the lock ring 66 is depicted in an embodiment of the disclosure. In some embodiments, the lock ring 66 includes a distal face 282 and a proximal face 284 separated by a perimeter portion 286. The distal face 282 may be convex and define a spherical profile 288. The proximal face 284 may include one or more malleable features 292 for engaging the base spinal support rod 36. The distal face 282 terminates at a distal edge 294 of the perimeter portion 286. In the depicted embodiment, a plurality of relief slots 296 are defined that are open at the distal edge 294 and extend axially into the perimeter portion 286. In some embodiments, the one or more malleable features 292 are plastically deformable. The one or more malleable features 292 may define a raised ridge 298, for example an annular ring as depicted in FIG. 24. In some embodiments, the lock ring 66 includes a radial detent 299 that extends radially outward from the perimeter portion 286.

Functionally, the convexity of the distal face 282 that accommodates and can slide over the spherical profile of the head portion 64 of the pedicle screw 22, thereby enabling the polyaxial movement of the base rod receptacle 24 relative to the head portion 64. The one or more malleable features 292 conform to the shape of the base spinal support rod 36 when the set screw 42 is tightened to secure the base spinal support rod 36 in place. The conformance of the malleable feature(s) 292 acts to grip the base spinal support rod 36, thereby inhibiting the base support rod 36 from rotating or sliding within the diametrically opposed slots 88 of the base rod receptacle 24. Upon tightening of the base set screw 42, the relief slots 296 enable the perimeter portion 286 to conform to the head portion 64 at the distal edge 294 for more effective gripping of the head portion 64 of the pedicle screw 22. The conformance of the malleable feature(s) 292 and perimeter portion 286 act to secure and inhibit movement between the head portion 64, the base spinal support rod 36, and the base rod receptacle 24. The radial detent 299 may interface with internal features 297 (FIG. 3) within the base rod receptacle 24, such as an internal inset flange (depicted) or optionally a groove (not depicted). The internal features 297 restrains the proximal face 284 from deflecting proximally (upward in FIGS. 2 and 3) when the lock ring 66 is deformed under the clamping force between the base spinal support rod 36 and the head portion 64, thereby maintaining gripping contact between the head portion 64 and the proximal face 284 of the lock ring 66.

Referring to FIGS. 25, 25A, 26, and 26A, threads defining a canted cantilever profile 450 and the advantage provided over conventional threaded arrangements are depicted and described according to embodiments of the disclosure. A conventional threaded arrangements 400, schematically depicted at FIGS. 25 and 25A, may include, for example, exterior threads 402 of a set screw 404 that are engaged with interior threads 406 of a wall segment 408 of a spinal rod receptacle 410 (akin to opposed wall segments 90 and 150 of the rod receptacles 24 and 34 of the extensible spinal support system 20). Both the set screw 404 and the wall segment 408 are concentric about a central axis 412 that defines the z-axis of a right-cylindrical coordinate system 424 having an axial coordinate z and a radial coordinate r. When the set screw 404 is tightened a first direction 416 to set against a spinal support rod 415, a clamping force vector FC is generated, for which there is an equal and opposite force vector FC' in a second direction 418 that is opposite the first direction 416. The force vector FC' in turn generates reaction force vectors FR generated at contact interfaces 422 between the exterior threads 402 of the set screw 404 and the interior threads 406 of the wall segment 408. The reaction forces FR generate an axial component FRZ and radial component FRR. Because of the standard shape of the threads 402 and 406, the radial components FRR generate a radial outward force FRO, i.e., away from the central axis 412.

For configurations such as the depicted extensible spinal support system 20, the wall segment 408 (e.g., wall segment 90 of the extensible spinal support system 20) is, in some embodiments, not supported by any structure. In such embodiments, the wall segment 408 will tend to cause deflections 6o that deflect radially outward in response to the radial outward force FRO. As the wall segment 408 deflects radially outward, the overlap between the threads 406 and 408 at the interfaces 422 is reduced, thereby weakening the coupling between the set screw 404 and the wall segment 408. The tighter the draw on the set screw 404, the greater the radial outward force FRO and the greater the deflection of the wall segment 408, further decreasing the overlap at the interfaces 422. Accordingly, as the torque requirements of the conventional set screw 404 are increased, the coupling between the set screw 404 and the wall segment 408 becomes more tenuous. Over time, creep stresses may cause the deflection of the wall segment 408 and the attendant decrease in the overlap at the interfaces 422, causing the clamping force FC to reduce. This can cause loosening of the assembly and slippage of the resident spinal rod within the spinal rod receptacle 410. In some instances, torque requirements can cause the set screw 404 to slip within the spinal rod receptacle 410 during implantation.

Figure 26:
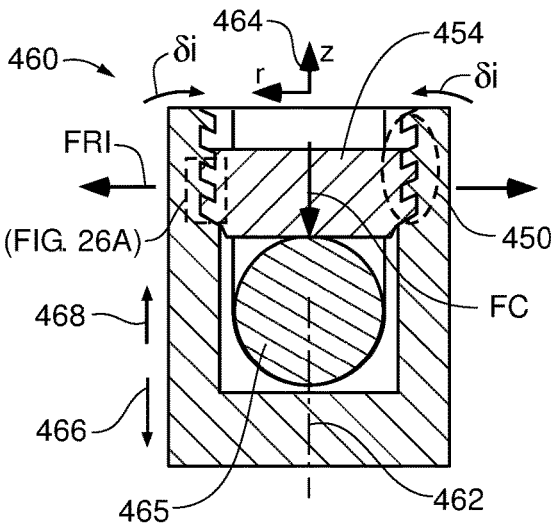
FIG. 26 is a sectional view of a rod receptacle in assembly having threads that define canted cantilever profile according to an embodiment of the disclosure.
Figure 26A:
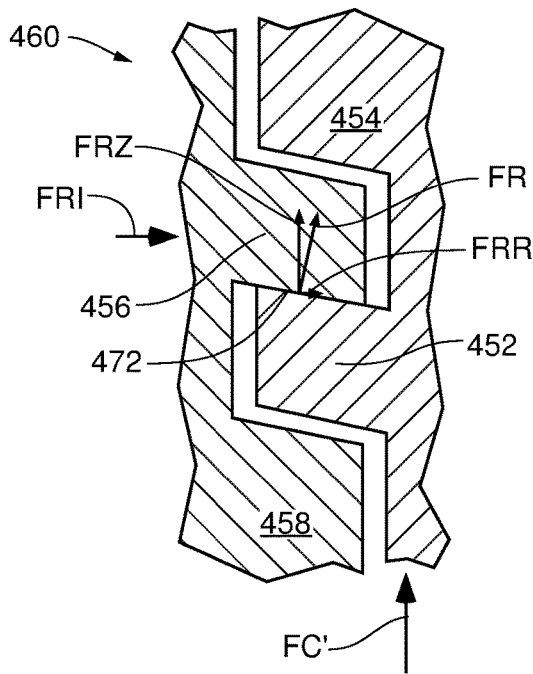
FIG. 26A is an enlarged, partial view of FIG. 26 according to an embodiment of the disclosure.

A threaded arrangement utilizing threads having the canted cantilever profile arrangement 450 is depicted at FIGS. 26 and 26A. The various threads 94, 96, 126, 154, 156, and 268 (FIGS. 2, 4, and 5) of the extensible spinal support system 20 may utilize a canted cantilever profile arrangement.

The canted cantilever profile arrangement 450, schematically depicted at FIGS. 26 and 26A, may include, for example, exterior threads 452 of a set screw 454 that are engaged with interior threads 456 of a wall segment 458 of a spinal rod receptacle 460 (akin to opposed wall segments 90 and 150 of the rod receptacles 24 and 34 of the extensible spinal support system 20). Both the set screw 454 and the wall segment 458 are concentric about a central axis 462 that defines the z-axis of a right-cylindrical coordinate system 464 having an axial coordinate z and a radial coordinate r. When the set screw 454 is tightened a first direction 466 to set against a spinal support rod 465, the clamping force vector FC is generated, for which there is the equal and opposite force vector FC' in a second direction 468 that is opposite the first direction 466. The force vector FC' in turn generates reaction force vectors FR generated at contact interfaces 472 between the exterior threads 452 of the set screw 454 and the interior threads 456 of the wall segment 458. The reaction forces FR generate an axial component FRZ and radial component FRR.

However, unlike the conventional threaded arrangements 400, the contact interfaces 472 of the canted cantilever profiles 450 are sloped radially inward (i.e., toward the central axis 462) in the first direction 466. By this arrangement, the radial component FRR is vectored inward, toward the center axis 466. The forces so generated will tend to cause deflections 6$i$ of the wall segment 458 that is radially inward in response to the radial inward force FRI. Because of the radial inward deflections 6$i$, the wall segments 458 tend to be supported by the set screw 454. Accordingly, the coupling between the set screw 454 and the spinal rod receptacle 460 provided by the canted cantilever profile arrangement 450 is stronger and can provide a greater clamping force FC than can the conventional threaded arrangement 400 of spinal rod receptacle 410.

For the extensible spinal support system 20, the interior threads 94, 154 of the base and extension rod receptacle 24, 34 interact with the set screws 42, 44 in the manner described attendant to the canted cantilever profile arrangement 450 of FIGS. 26 and 26A. The exterior threads 96, 156 of the base and extension rod receptacle 24, 34 may also implement a canted cantilever arrangement (see, e.g., FIGS. 2, 4, and 5), but may be configured to generate different forces and deflections. For example, the exterior threads 96, 156 of the base and extension rod receptacle 24, 34 are sloped radially outward (i.e., away the central axis 462) in the distal direction 74. By this arrangement, the radial components of the reaction forces at the interface of the exterior threads 96, 156 and the interior threads 126, 226 of the skirt portions 124, 224 is vectored outward, away from the center axis 67. The forces so generated will tend to cause splaying of the rod receptacle 24, 34, i.e., to cause the wall segments 90, 150 to deflect radially outward. Because of the radial outward deflections, the wall segments 90, 150 tend to be supported by the skirt portions 124, 224. The skirt portions 124, 224, being tangentially continuous, incurs a hoop stress that further counters the outward radial forces and limits splaying. The outward radial forces at the exterior threads 96, 156 also tend to counter and can be tailored to balance the inward radial forces FRI to further reduce overall radial deflection (splaying) and deformation of the wall segments 90, 150.

Figure 25:
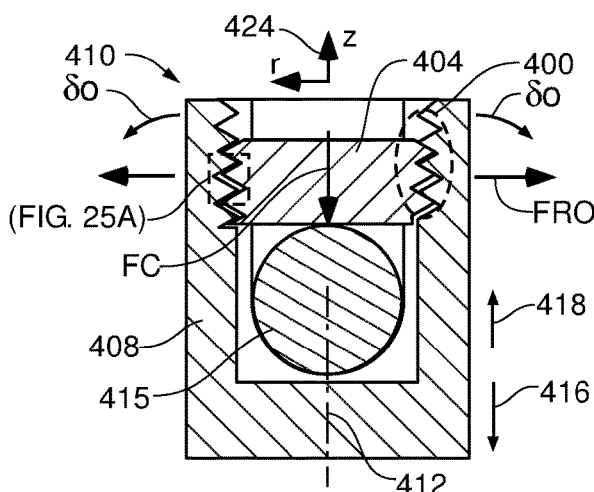
FIG. 25 is a sectional view of a conventional rod receptacle in assembly.
Figure 25A:
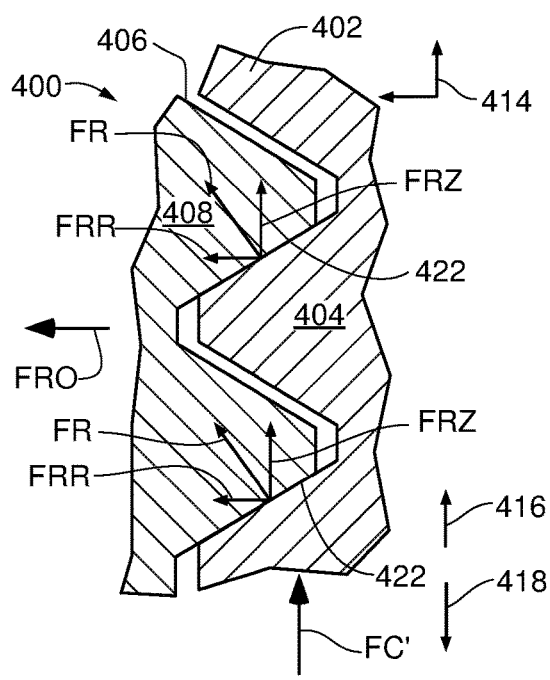
FIG. 25A is an enlarged, partial view of FIG. 25.

Alternatively, the exterior threads 96, 156 of the receptacles 24, 34 and the interior threads 126, 226 of the skirt portions 124, 224 may be of a conventional arrangement. Conventional threads, as described attendant to FIGS. 25 and 25A, provide radial outward forces that are subsequently supported by the skirt portions 124, 224 and as a counter to the radial inward force FRI, to prevent splaying.

Each of the additional figures and methods disclosed herein can be used separately, or in conjunction with other features and methods, to provide improved devices and methods for making and using the same. Therefore, combinations of features and methods disclosed herein may not be necessary to practice the disclosure in its broadest sense and are instead disclosed merely to particularly describe representative and preferred embodiments.

Various modifications to the embodiments may be apparent to one of skill in the art upon reading this disclosure. For example, persons of ordinary skill in the relevant arts will recognize that the various features described for the different embodiments can be suitably combined, un-combined, and re-combined with other features, alone, or in different combinations. Likewise, the various features described above should all be regarded as example embodiments, rather than limitations to the scope or spirit of the disclosure.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

Unless indicated otherwise, references to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

What is claimed is:

1. A spinal support system, comprising:
  a first rod receptacle for mounting to a pedicle screw, said first rod receptacle having a first side wall that includes a first interior surface and a first exterior surface, said first side wall defining a first pair of diametrically opposed slots that extend axially along said first side wall and are open at a proximal end of said first rod receptacle, said first interior surface defining first interior threads, said first exterior surface defining first exterior threads; and
  an extension assembly including a second rod receptacle mounted to a base portion, said second rod receptacle including an internal flange having an interior face and defining an axial thickness, said base portion including a mounting platform and a skirt portion that extends from said mounting platform, said skirt portion including interior threads for mating with said first exterior threads of said first rod receptacle, said second rod receptacle having a second side wall that includes a second interior surface and a second exterior surface, said second side wall defining a second pair of diametrically opposed slots that extend axially along said second side wall and are open at a proximal end of said second rod receptacle, said second interior surface defining second interior threads, wherein said extension assembly includes a pivot member that attaches said second rod receptacle to said base portion, said pivot member including a head portion and a shaft portion, said shaft portion including a stop that cooperates with said base portion to define a predetermined axial gap dimension between said head portion and said mounting platform of said base portion, said shaft portion being in fixed relationship with said mounting platform, said head portion of said pivot member being dimensioned to extend over said interior face of said internal flange to couple said second rod receptacle and said base portion, said axial gap being greater than said axial thickness of said internal flange to enable monoaxial rotation of said extension rod receptacle about said pivot head portion.

2. The spinal support system of claim 1, wherein:
said second rod receptacle defines an opening at a distal end thereof, said opening sized to accommodate passage of said shaft portion of said pivot member; and
said mounting platform of said base portion defines a center hole for receiving said pivot member.

3. The spinal support system of claim 2, wherein said shaft portion includes external shaft threads formed on an exterior surface thereof, and said center hole includes interior threads for mating with said external shaft threads.

4. The spinal support system of claim 2, wherein said shaft portion is right cylindrical and includes a smooth exterior surface, and said center hole is right cylindrical and dimensioned for a sliding fit with said shaft portion.

5. The spinal support system of claim 2, wherein said shaft portion is welded to said base portion.

6. The spinal support system of claim 2, wherein said shaft portion is swaged to said base portion.

7. The spinal support system of claim 1, wherein:
said head portion of said pivot member is one of a flat head and a countersink head; and
said interior face of said internal flange of said second rod receptacle is machined to conform to said head portion to enable selective monoaxial rotation about said head portion.

8. The spinal support system of claim 1, wherein a set screw portion is integral with and extends from a distal face of said mounting platform, said set screw portion including threads configured to mate with said first interior threads of said first rod receptacle.

9. The spinal support system of claim 8, wherein said threads of said set screw portion and said first interior threads of said first rod receptacle define canted cantilever profiles configured to threadably engage each other.

10. The spinal support system of claim 1, wherein said second exterior surface of said second rod receptacle includes second exterior threads.

11. The spinal support system of claim 10, comprising a cap including a skirt portion having interior threads for mating with said second exterior threads of said second rod receptacle.

12. The spinal support system of claim 1, wherein said first exterior threads and said interior threads of said skirt portion define canted cantilever profiles configured to threadably engage each other.

13. A spinal rod support system, comprising:
an extension rod receptacle including an internal flange at a distal end, said internal flange defining an axial thickness;
a base portion including a mounting platform that defines a center hole accessible from a proximal face of said mounting platform;
a pivot member including a head portion and a stop, said stop registering against said proximal face of said platform to define a predetermined axial gap dimension between said head portion and said mounting platform that is greater than said axial thickness of said internal flange of said extension rod receptacle; and
means for coupling said pivot member to said base portion,
wherein said internal flange of said extension rod receptacle is captured between said head of said pivot member and said proximal face of said mounting platform, said extension rod receptacle being monoaxially rotatable about said head portion.

14. The spinal support system of claim 13, wherein said means for coupling said extension rod receptacle to said base portion includes said pivot member threadably engaged with said center hole.

15. The spinal support system of claim 13, wherein said means for coupling said extension rod receptacle to said base portion includes said pivot member swaged to said center hole.

16. The spinal support system of claim 13, wherein said means for coupling said extension rod receptacle to said base portion includes said pivot member fused to said center hole.

17. The spinal support system of claim 16, wherein said pivot member is welded to a periphery of said center hole at a distal face of said base portion.

18. The spinal support system of claim 13, comprising:
a base rod receptacle; and
means for coupling said base portion to said base rod receptacle.

19. The spinal support system of claim 18, wherein:
said base portion includes a skirt portion; and
said means for coupling said base portion to said base rod receptacle includes threaded engagement of said skirt portion to said base rod receptacle.

20. The spinal support system of claim 19, wherein:
said base portion includes a set screw portion that is unitary with and extends from a distal face of said mounting platform; and
said means for coupling said base portion to said base rod receptacle includes threaded engagement of said set screw portion to said base rod receptacle.

* * * * *